United States Patent
Kim et al.

(10) Patent No.: US 9,708,378 B2
(45) Date of Patent: Jul. 18, 2017

(54) PEPTIDES DERIVED FROM NCAPG2 AND THEIR USE

(71) Applicant: NATIONAL CANCER CENTER, Goyang-si, Gyeonggi-do (KR)

(72) Inventors: Kyungtae Kim, Seoul (KR); Byung Il Lee, Goyang-si (KR); Jae Hyeong Kim, Bucheon-si (KR)

(73) Assignee: NATIONAL CANCER CENTER, Goyang-si (KR)

( * ) Notice: Subject to any disclaimer, the term of this patent is extended or adjusted under 35 U.S.C. 154(b) by 0 days.

(21) Appl. No.: 15/285,873

(22) Filed: Oct. 5, 2016

(65) Prior Publication Data

US 2017/0014480 A1 Jan. 19, 2017

Related U.S. Application Data

(60) Division of application No. 15/185,796, filed on Jun. 17, 2016, now Pat. No. 9,562,084, which is a continuation-in-part of application No. 14/340,250, filed on Jul. 24, 2014, now abandoned.

(30) Foreign Application Priority Data

Jan. 15, 2014 (KR) ......................... 10-2014-0005149
Jul. 15, 2014 (KR) ......................... 10-2014-0089159

(51) Int. Cl.
*C07K 14/47* (2006.01)
*A61K 38/17* (2006.01)
*G01N 33/50* (2006.01)
*C12N 9/12* (2006.01)
*A61K 38/00* (2006.01)

(52) U.S. Cl.
CPC ...... *C07K 14/4702* (2013.01); *A61K 38/1709* (2013.01); *C07K 14/47* (2013.01); *C12N 9/1205* (2013.01); *C12Y 207/11021* (2013.01); *G01N 33/5011* (2013.01); *A61K 38/00* (2013.01); *C07K 2319/23* (2013.01); *C07K 2319/43* (2013.01); *C07K 2319/50* (2013.01); *C07K 2319/60* (2013.01); *G01N 2333/4703* (2013.01); *G01N 2333/4706* (2013.01); *G01N 2333/912* (2013.01); *G01N 2440/14* (2013.01)

(58) Field of Classification Search
CPC ..................... C07K 14/4702; A61K 38/1709
See application file for complete search history.

(56) References Cited

PUBLICATIONS

NCBI Reference Sequence: NP_060230.5, condensin-2 complex subunit G2 isoform a [*Homo sapiens*], Jan. 11, 2014, available at: www.ncbi.nlm.nih.gov/protein/116812586?sat=18&satkey=2751993.
UniProtKB. Q86XI2 (CNDG2_HUMAN). 2003.
Sigma-Aldrich. Serine/Threonine Kinase Inhibitors. 2009.
Steegmaier et al. Current Biology. 17, 316-322. 2007.
Published on Feb. 20, 2013 under the title of "Condensin complex role in microtubule kinetochore interaction", The first round table discussion at Cell Cycle Symposium 2013 of Korean Society of Molecular and Cellular Biology.
Published on Jun. 30, 2013 under the title of "Functional Identification of Condensin Complex in Cell Cycle Regulation", Dissertation for the Degree of Doctor of Philosophy by Jae Hyeong Kim, The Graduate School Sookmyung Women's University.
Published on Jul. 6, 2013 under the title of "Structural and functional studies of condensin association with histone", Research report of 2013 year, Ministry of Science, ICT and Future Planning.
Ryu et al., "Comprehensive Expression Profiling of Tumor Cell Lines Identifies Molecular Signatures of Melanoma Progression", PLoS One. 2007, vol. 2, Issue 7, e594.
Shiheido et al., "An Anilinoquinazoline Derivative Inhibits Tumor Growth through Interaction with hCAP-G2, a Subunit of Condensin II", PLoS One. 2012, vol. 7, Issue 9, e44889.

*Primary Examiner* — Amber D Steele
(74) *Attorney, Agent, or Firm* — Vorys, Sater, Seymour & Pease LLP; Mih Suhn Koh

(57) ABSTRACT

NCAPG2, a component of condensin complex II, protein and novel peptides derived from the protein are provided. The peptide may include a fragment of the NCAPG2 protein. The peptide may be a peptide including a fragment of NCAPG2 protein having the amino acid sequence of SEQ ID NO: 7, wherein the fragment includes the amino acid residue number 805 or 1010 of SEQ ID NO: 7, a peptide having the sequence of SEQ ID NO: 8, or a peptide having the sequence of SEQ ID NO: 11. The protein or peptides can be used for preparing and screening pharmaceutical compositions for treating diseases or disorders associated with abnormal cell division including cancer.

3 Claims, 38 Drawing Sheets

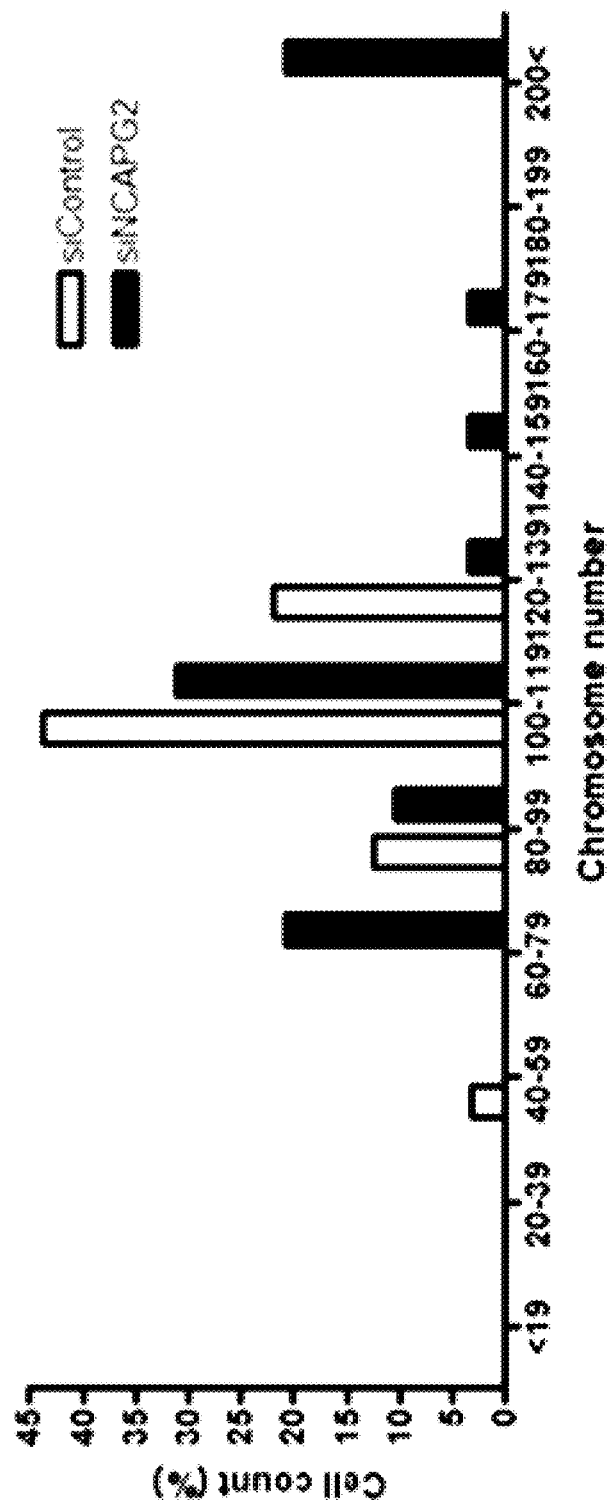

Bar:5μm

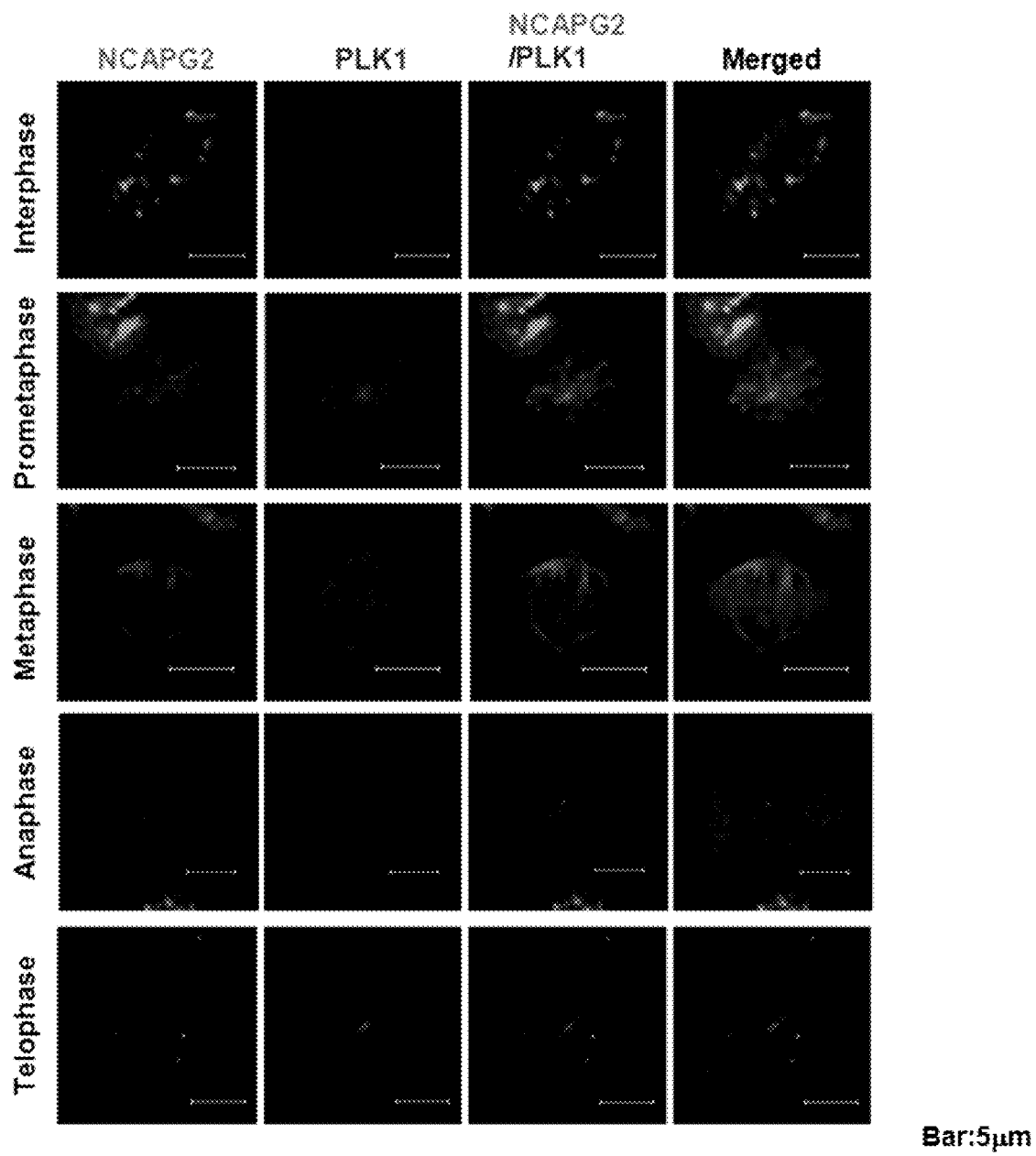

FIG. 6B
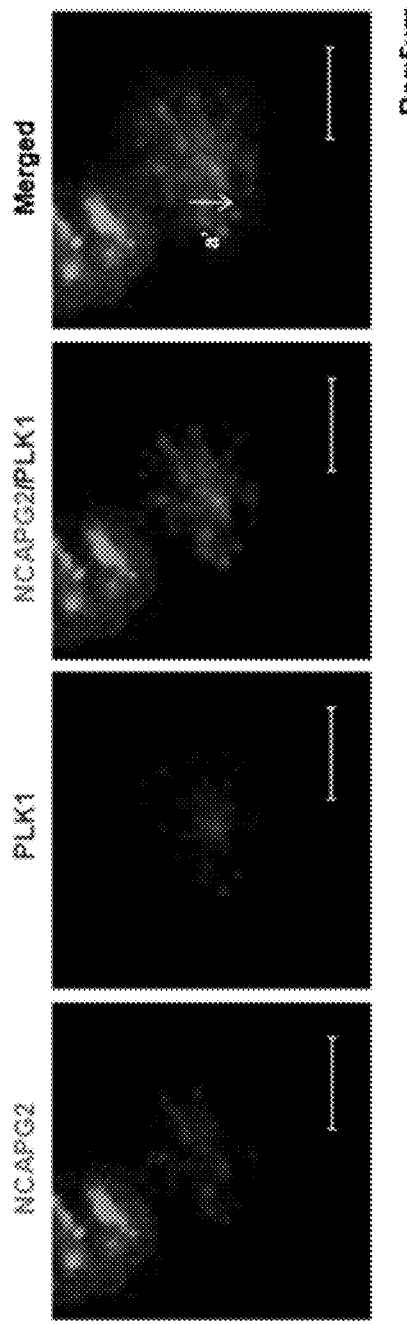
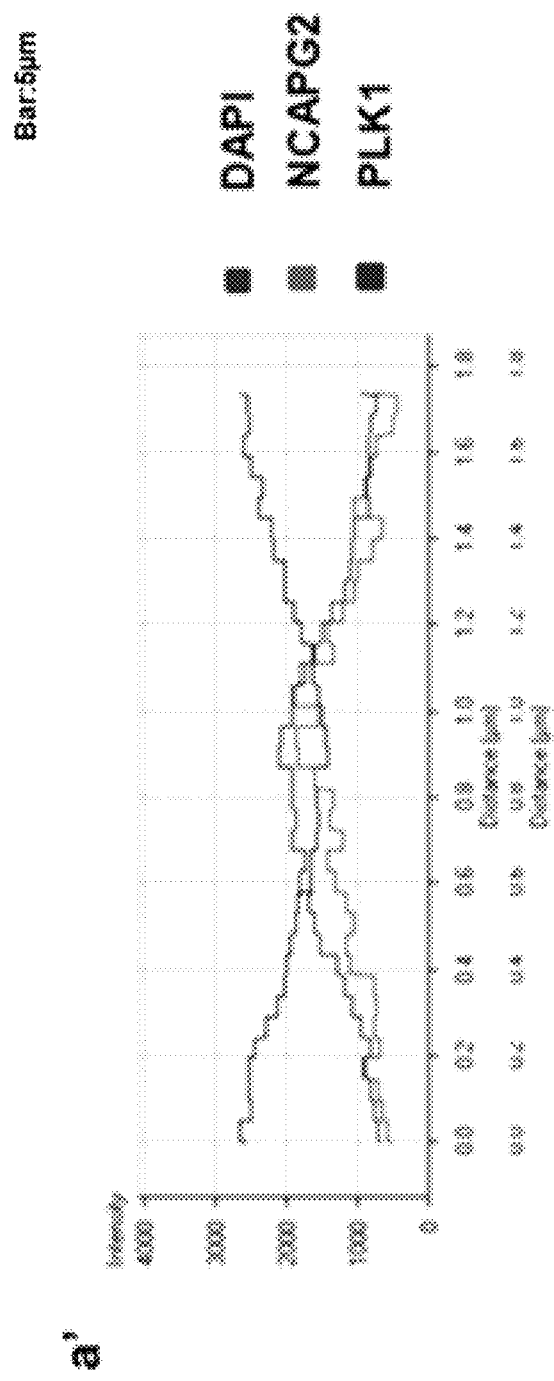

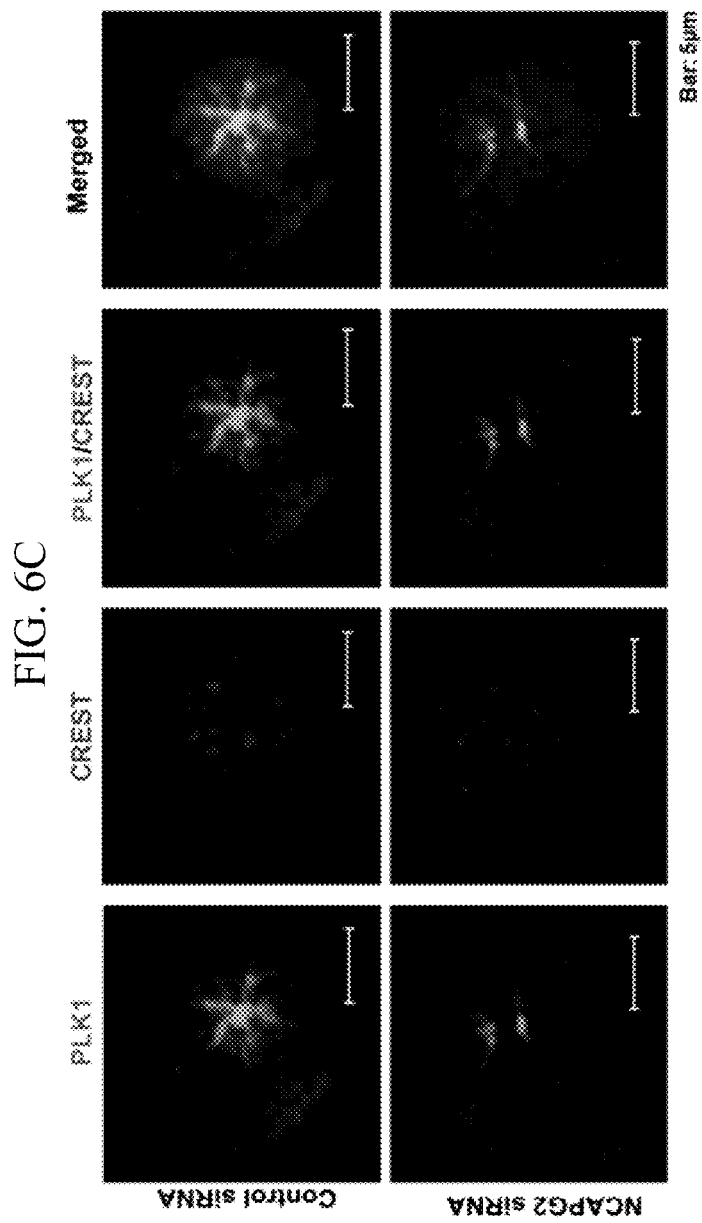

━━ NCAPG2 (VLS-pT-L)   ━━ PBIP (LHS-pT-A)
━━ synthetic (MQS-pT-PL)   ━━ Cdc25C (LLCS-pT-PN)

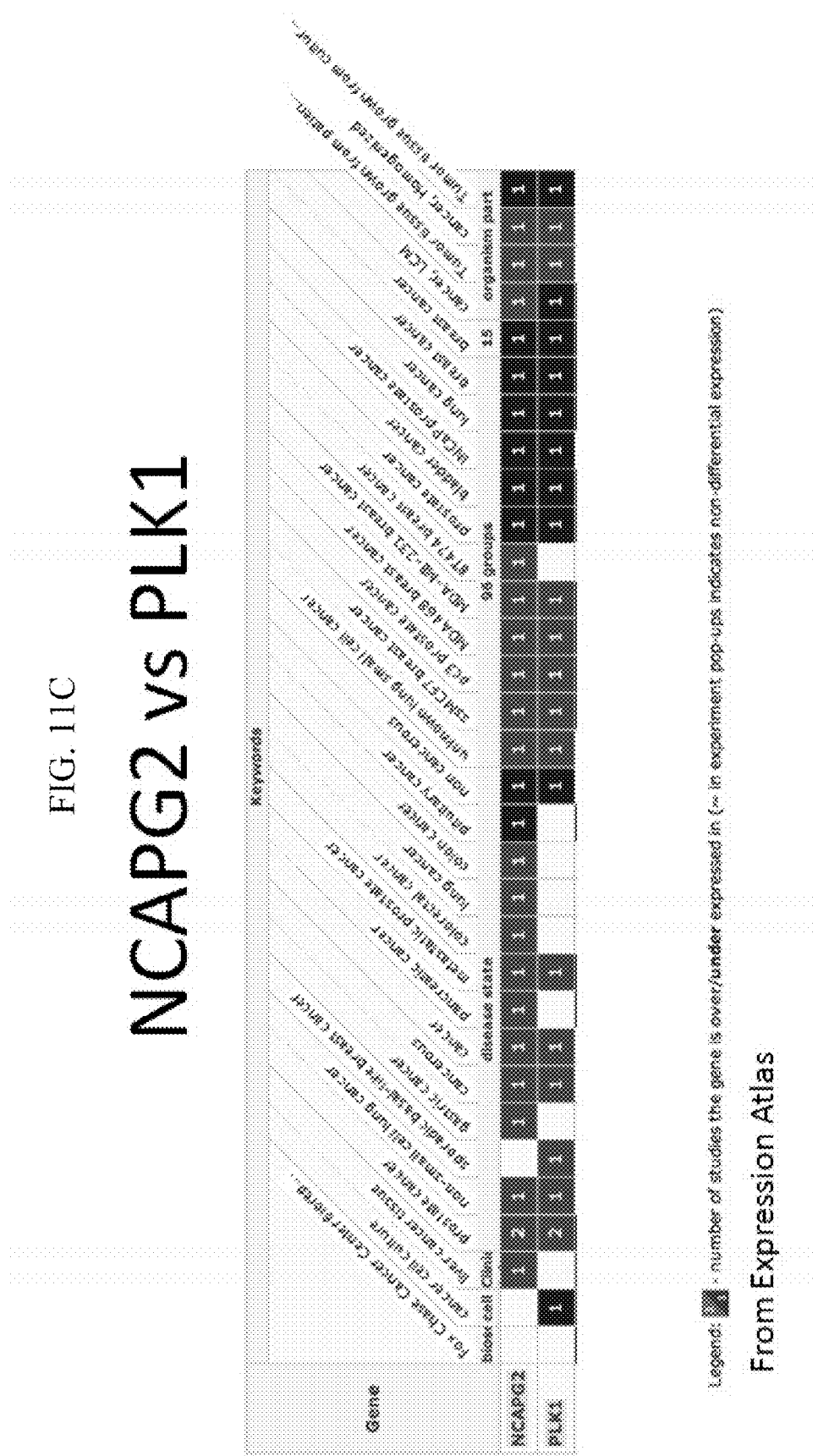

FIG. 11D
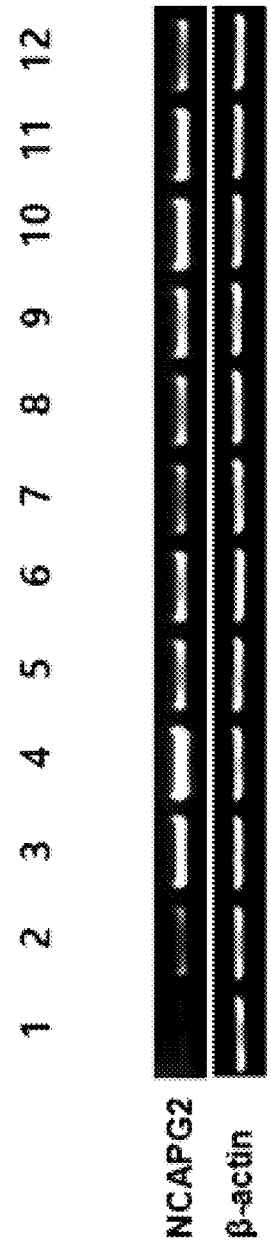 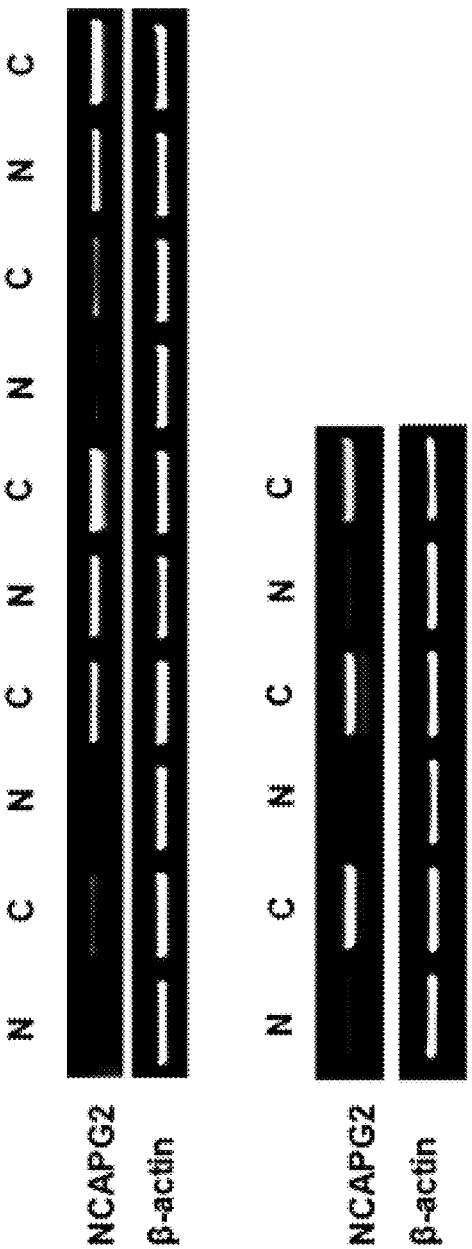

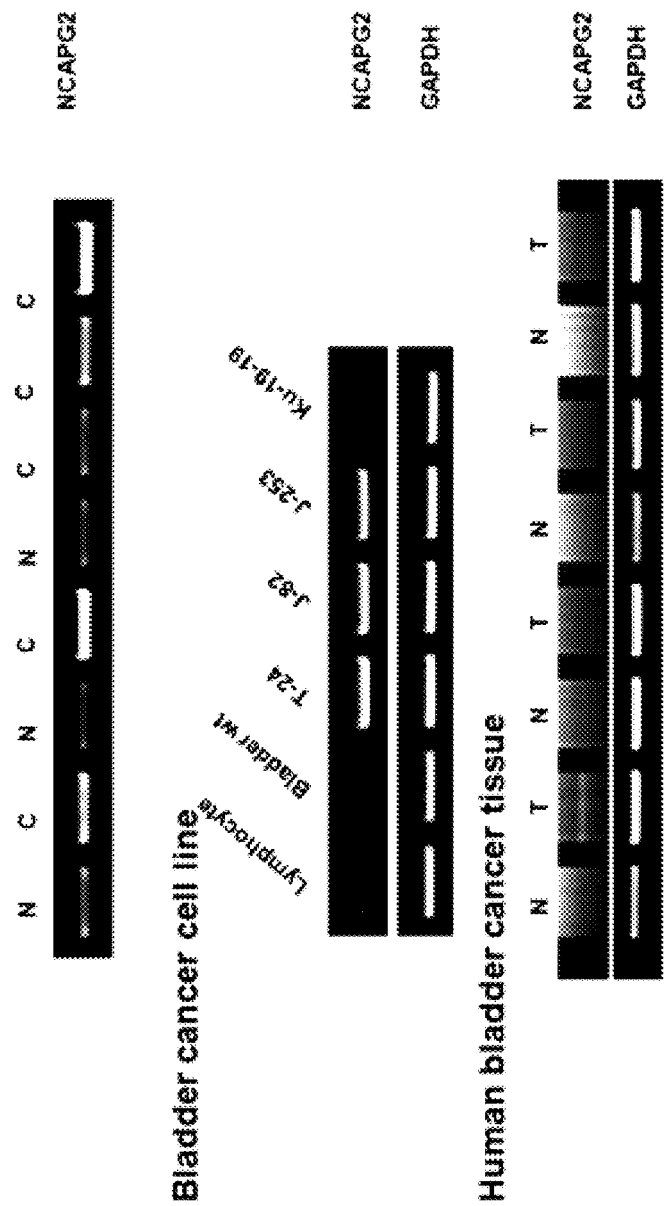

FIG. 14
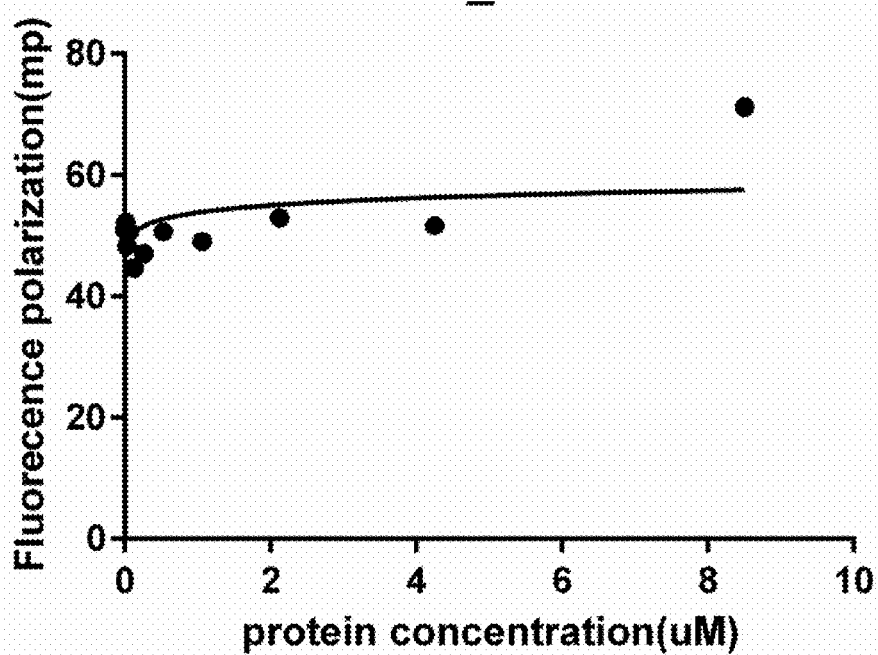
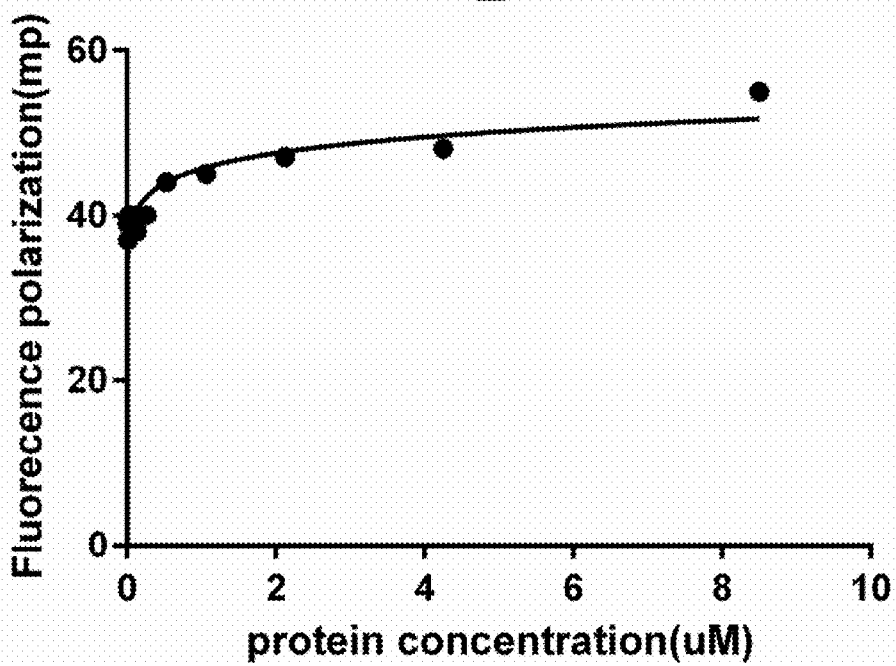

PEPTIDES DERIVED FROM NCAPG2 AND THEIR USE

CROSS REFERENCE TO RELATED APPLICATIONS

This application is a Divisional of U.S. patent application Ser. No. 15/185,796 filed on Jun. 17, 2016, which was a Continuation-In-Part Application of U.S. patent application Ser. No. 14/340,250, filed Jul. 24, 2014, which claims the benefit of Korean Patent Application No. 10-2014-0005149, filed Jan. 15, 2014 and Korean Patent Application No. 10-2014-0089159, filed Jul. 15, 2014, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing named "SequenceListing.TXT", created on Aug. 16, 2016, 11.6 KB, and is part of the specification and is herein incorporated by reference in its entirety.

FIELD OF THE INVENTION

The present invention relates to NCAPG2, a component of condensin complex II, protein implementing chromosome segregation through microtubule-kinetochore attachment by PLK1 recruitment in prometaphase kinetochore. Provided are NCAPG2 and novel peptides derived from the protein. The protein and peptides are useful in preparing and screening pharmaceutical compositions for treating diseases or disorders associated with abnormal cell division including cancer.

BACKGROUND OF THE INVENTION

Chromosome condensation during the mitosis is critical for proper bi-oriented chromosome separation (Hirano 2012; Thadani et al. 2012). The production of this mitosis-specific chromosome structure depends mainly on three multi-protein complexes: two condensin complexes and one cohesion complex (Wood et al. 2010). Each condensin complex is composed of two ATPase subunit heterodimers (structural maintenance of chromosomes (SMC) 2 & 4) and three non-SMC regulatory subunits (Wood et al. 2010; Hirano 2012). A unique set of three non-SMC regulatory components defines each condensin complex, NCAP-D2, NCAP-G, and NCAP-H are parts of condensin complex I, and NCAP-D3, NCAP-G2, and NCAP-H2 are components of condensin complex II (Wood et al. 2010; Green et al. 2012; Hirano 2012). NCAPG and NCAPD2 in condensin I, and NCAPG2 and NCAPD3 in condensin II are HEAT-repeat-containing regulatory subunits (Neuwald and Hirano 2000). Condensin complex I, which has a conserved structure in yeast and eukaryotes, is considered a canonical condensin complex for the condensation of eukaryotic chromosomes (Hirano 2012). Condensin complex II regulates not only chromosome condensation, but also diverse cellular functions, including chromosome segregation, DNA repair, sister chromatid resolution, gene expression regulation, and histone modulation (Hagstrom et al. 2002; Stear and Roth 2002; Ono et al. 2004; Smith et al. 2004; Xu et al. 2006; Wood et al. 2008; Csankovszki et al. 2009; Samoshkin et al. 2009; Liu et al. 2010; Floyd et al. 2013; Ono et al. 2013). Interestingly, homozygous mutants of all nematode condensin complex II components show nuclei of abnormal sizes or uneven distribution (Csankovszki et al. 2009). In human cells, the depletion of any components of condensin complex II also results in defects in chromosome alignment or segregation (Ono et al. 2004). Besides, the manner of regulation of chromosome segregation by each condensin component is dissimilar. While NCAPD3 depletion has a major effect on centrosome separation, NCAPG2 depletion appears more frequently as misaligned chromosomes in the metaphase plate (Ono et al. 2004). Recent studies have begun to address how each condensin components control regulatory function for the mitosis progress. For chromosome segregation in particular, recent reports have shown that NCAPD3 contributes to PLK1 loading in the chromosome arm. However, the detailed mechanical feature of each condensin complex II component regulating chromosome segregation is not known. Particularly, condensin complex II localized in kinetochore relative to condensin complex I (Hirota et al. 2004), the function of condensin complex II component in kinetochore for chromosome segregation is remained to dissolve.

The first step of chromosome segregation is the microtubule attachment to the kinetochore on the chromosome (Foley and Kapoor 2013). The kinetochore is the protein complex assembly that corresponds to the centromere of the chromosome where sister chromatids are linked (Foley and Kapoor 2013). The microtubule-kinetochore interactions require precise control to achieve the correct bi-oriented interaction. The early event of microtubule attachment to the kinetochore prior to the stabilization of interactions is governed by Polo-like kinase 1 (PLK1) (Barr et al. 2004; Lens et al. 2010; Carmena et al. 2012; Liu et al. 2012a; Foley and Kapoor 2013). PLK1 localizes diversely during mitosis according to the microtubule movement, from the centrosome to the kinetochore and then to the midbody (Lee et al. 1998; Barr et al. 2004; Lens et al. 2010). PLK1 localizes in the kinetochore until chromosome alignment is completed in the metaphase plate (Lens et al. 2010). When each kinetochore is not occupied properly by a microtubule, kinetochore-localized PLK1 phosphorylates BubR1, awaiting the onset of anaphase (Lampson and Kapoor 2005; Elowe et al. 2007; Matsumura et al. 2007; Liu et al. 2012a; Suijkerbuijk et al. 2012). Although it has been reported that some proteins in the kinetochore are responsible for PLK1 localization to the kinetochore, further research is needed to determine which substrate contributes to microtubule-dependent temporal and spatial rearrangements at the centromere to achieve microtubule binding (Foley and Kapoor 2013).

Here, we investigated the function of NCAPG2 in chromosome segregation during mitosis using *C. elegans*, a nematode model, and a human cell line. Our results demonstrate that NCAPG2 contributes to chromosome segregation by microtubule-kinetochore attachment regulation mediating PLK1 localization at the kinetochore. This function of NCAPG2 is conserved in both nematodes and mammals and is essential for achieving chromosome integrity in cell division.

SUMMARY

In one aspect, the present invention provides NCAPG2 protein having the amino acid sequence of SEQ ID NO: 7 and peptides comprising a fragment of the NCAPG2 protein. In one embodiment, the fragment comprises the amino acid residue number 805 or 1010 of SEQ ID NO: 7, or the sequence of SEQ ID NO: 8 or SEQ ID NO: 11. In one embodiment, the NCAPG2 protein can be obtained from human.

In another aspect, the present invention provides a pharmaceutical composition comprising NCAPG2 protein; a peptide comprised of a fragment of the NCAPG2 protein; a polynucleotide encoding the protein or the peptide; or a suppressor (or inhibitor) suppressing expression or activity of the protein, peptide or polynucleotide. In one embodiment, the fragment comprises the amino acid residue number 805 or 1010 of SEQ ID NO: 7, or the sequence of SEQ ID NO: 8 or SEQ ID NO: 11. In one embodiment, the suppressor comprises a mutator nucleotide sequence that mutates the amino acid residue 805 or 1010 of SEQ ID NO: 7. In one embodiment, the mutator nucleotide sequence that mutates the amino acid residue 1010 of SEQ ID NO: 7 comprises a primer of SEQ ID NO: 5 or SEQ ID NO: 6. In one embodiment, the mutator nucleotide sequence that mutates the amino acid residue 805 of SEQ ID NO: 7 comprises a primer of SEQ ID NO: 9 or SEQ ID NO: 10. In another embodiment, the suppressor suppresses phosphorylation of amino acid residue 1010 of SEQ ID NO: 7. In one embodiment, the suppressor is a single organic compound, a single inorganic compound, a biopolymer including peptide, protein, nucleic acid or lipid, or a complex compound. In one embodiment, the pharmaceutical composition is an antitumor agent.

In another aspect, the present invention provides a method of screening an antitumor agent, comprising: preparing a cell or an animal expressing NCAPG2 protein or a peptide derived from the NCAPG2 protein; treating the cell or the animal with a substance specifically interacted with the protein, the peptide or a polynucleotide encoding the protein or peptide; and determining whether the protein or the peptide binds to PLK1 (polo-like kinase 1). In one embodiment, the peptide comprising a fragment of NCAPG2 protein having the amino acid sequence of SEQ ID NO: 7. In one embodiment, the fragment comprises the amino acid residue number 805 or 1010 of SEQ ID NO: 7, or the sequence of SEQ ID NO: 8 or SEQ ID NO: 11. In one embodiment, the substance is a single organic compound, a single inorganic compound, a biopolymer including peptide, protein, nucleic acid or lipid, or a complex compound. For example, the substance comprises siRNA, antisense oligonucleotide, ribozyme, antibody, aptamer, spiegelmer, or a combination thereof. In another embodiment, the determining step comprises an immunoprecipitation method or fluorescence polarization assay.

NCAPG2 protein or peptides according to the present invention can be a novel target for inhibiting cell division. Therefore, the pharmaceutical composition comprising or suppressing the NCAPG2 protein or peptide according to the present invention can show anti-tumor activity by arresting cell cycle or inducing apoptosis. Also, the screening method using the NCAPG2-PLK1 binding according to the present invention can be a useful tool for developing a novel anti-tumor agent.

BRIEF DESCRIPTION OF THE DRAWINGS

FIG. 1A: Images of somatic mitosis in control or capg-2 RNAi fed adult parent in a strain carrying GFP::histone H2B to visualize chromosome. FIG. 1B: Images of embryonic mitosis after spindle polarity toxin (nocodazole and taxol) treatment in control or capg-2 depletion RNAi fed adult parent in a strain carrying GFP::histone H2B to visualize chromosome. FIG. 1C: Quantitative analysis of embryonic survivals after nocodazole and taxol treatment in either control or capg-2 RNAi fed adult parent carrying H2B::GFP strain. FIG. 1D: Time lapse images of chromosome segregation during mitosis in embryo from either control or capg-2 RNAi fed adult worm carrying H2B and Histone fluorescence fusion protein strain. FIG. 1E: Chromosome alignments and uneven chromosome microtubule attachments defects with capg-2 depletion in C. elegans.

FIGS. 2A to 2C illustrate NCAPG2 stabilizes microtubule-kinetochore interactions for proper chromosome segregation in human cells. FIG. 2A: Kinetochores and microtubule were visualized with staining against anti-CREST or anti-tubulin antibody in either control or NCAPG2 siRNA delivered cells. FIG. 2B: Images of centromere FISH signals and DAPI staining were captured. FIG. 2C: Chromosome numbers were counted in control or NCAPG2 siRNA treated cells.

FIG. 3A: CREST and bubR1 were immunostained and visualized as pseudo-color images obtained with the confocal microscopes. Enlarged images in squares indicate BubR1 localization at the kinetochore end. FIG. 3B: Immunoblotting of each indicated antibodies, using the subject either control or NCAPG2 siRNA treatments cell lysates. FIG. 3C: BubR1 and PLK1 were immunostained and visualized as pseudo-color confocal microscope images of control or NCAPG2 siRNA-treated cells. The fluorescence intensity of each indicated spot was calculated from microscopes images.

FIG. 5 illustrates PLK1 localization during cell cycle detected from immunostaining.

FIGS. 6A to 6F illustrates NCAPG2 is required for PLK1 localization to kinetochores. FIG. 6A: NCAPG2 localization at chromosome in prometaphase cell detected from NCAPG2 and/or CREST immunostaining and their fluorescence intensities. FIG. 6B: Co-localization of NCAPG2 and PLK1 in prometaphase cell detected from NCAPG2 and/or CREST immunostaining and their fluorescence intensities. FIG. 6C: PLK1 localization at the kinetochore was detected from PLK1 and/or CREST immunostaining in control or NCAPG2 siRNA treated cell. FIG. 6D: Co-localization coefficients were calculated from the intensities of PLK1 and CREST images and represented as the mean±S.E. from the total sum of three independent experiments. FIG. 6E: PLK1 localization was detected after control or CAPG-2 depletion using the transgenic C. elegans expressing GFP::PLK-1 fusion protein. FIG. 6F: The intensities of GFP::PLK-1 at the kinetochore and centrosome were measured separately, and each ratio was calculated in each cell from either controls or CAPG-2-depleted cells using C. elegans expressing GFP::PLK-1. CAPG-2 depletion significantly reduced the level of GFP::PLK-1 at chromosomes.

FIG. 7A: Immuno-precipitation with Flag or GST bead was performed in Flag-NCAPG2 and GST-PLK1 transfected cells and immune-blot was conducted using reversed antibodies. FIG. 7B: Detection of endogenous PLK1 binding into NCAPG2 was shown using immune-precipitation with Flag bead in Flag-NCAPG2 transfected cells. FIG. 7C: Schematic illustration of the PLK1 mutants vectors for immunoprecipitation assay. FIG. 7D: Each PLK1 mutants were immunoprecipitated by Flag beads, and NCAPG2 was detected with immunoblotting in each Flag-PLK1 mutants transfected cells. Each Flag-PLK1 mutant transfected-cell was subjected to immunoprecipitation using Flag bead, and NCAPG2 was detected by immunoblotting.

FIG. 8A: Each NCAPG2 deletion mutant (NCAPG2(1-543), NCAPG2(1-713) and NCAPG2(1-1143)) immunoprecipitated by Flag beads and PLK1 was detected by immunoblotting in each Flag-NCAPG2 mutant transfected cells. FIG. 8B: Scheme illustrating of the possible binding motif for the PBD in C-terminal of NCAPG2. FIG. 8C: Results of fluorescence polarisation for monitoring the binding of FITC-labelled peptides to the PBD of PLK1. The 1010pT peptide is shown in orange, and the non-phosphorylated 1010 peptide is shown in green. The data are presented as the mean±SD of triplicates of three independent experiments. FIG. 8D: Immunoprecipitation of wild type or T1010A mutant of Flag-tagged NCAPG2 with GST-tagged PLK1 and immunoblotting was performed using anti-GST antibody. FIG. 8E: NCAPG2 The1010 phosphoryated and p-1010T NCAPG2 localized on chromosome and kinetochore in mitosis. NCAPG2 pThe1010 antibody was made in rabbit with VLSpTL-containing peptide as antigen. Phosphoryated T1010-NCAPG2 detected with western blotting and localization images captured using a confocal microscope (Cal-Zeiss) after immunofluorescence staining. FIG. 8F: Immunoprecipitation of wild type, T805A or T1010A mutant of Flag-tagged NCAPG2 with GST-tagged PLK1 and immunoblotting was performed using anti-GST antibody.

FIG. 10A: Lentivirus expressing the siRNA-resistant mock, wild-type or T1010A mutant NCAPG2$^R$ infected in NCAPG2 siRNA-transfected cells. PLK1 and CREST stained in wild-type or T1010A NCAPG2$^R$ mutated lentiviral reconstituted cells. FIG. 10B: Co-localization coefficients were calculated from the intensities of PLK1 and CREST staining in mock, wild-type or T1010A NCAPG2$^R$ lentiviral reconstituted cells and represented as the mean±S.E. of the total sum of three independent experiments. FIG. 10C: Model of NCAPG2 and PLK1 binding at kinetochores for proper microtubule-kinetochore assembly. In the presence of NCAPG2, PLK1 is recruited to the kinetochore and phosphorylates BubR1, the PLK1 substrate at the kinetochore, which is required for precise chromosome segregation. Surveillance of proper microtubule-kinetochore assembly is activated, and microtubule-kinetochore attachments are fully satisfied before segregation. However, without NCAPG2, PLK1 localization and BubR1 phosphorylation are disrupted at the kinetochore. Therefore, NCAPG2 is necessary for proper PLK1 recruitment to the kinetochore and for precise chromosome segregation.

FIGS. 11A to 11E illustrate expression levels of NCAPG2 in cancer cell lines or tissues. FIGS. 11A, 11B and 11D: breast cancer cell lines or tissues. FIG. 11E: colon and bladder cancer cell lines or tissues. FIG. 11C: Result of Expression Atlas database.

FIGS. 13 and 14 illustrate 1010pT peptide (GVLSpTLI) specifically binds to PLK1.

DETAILED DESCRIPTION

Condensin complexes have pivotal functions during mitotic chromosome condensation. Although the role of the condensin complexes in chromosome segregation is highly conserved from nematodes to mammals, little is known concerning the specific components of the condensin I or II complex that drive chromosome segregation and how these components function in the diverse steps of chromosome segregation. PLK1 localization at the kinetochore is essential for microtubule-kinetochore attachments and for reliable chromosome segregation. In the present invention, we have shown that NCAPG2, which is one of the components of the non-SMC condensin II complex, may contribute to chromosome segregation by recruiting PLK1 to the kinetochore during prometaphase.

Figure 1A:
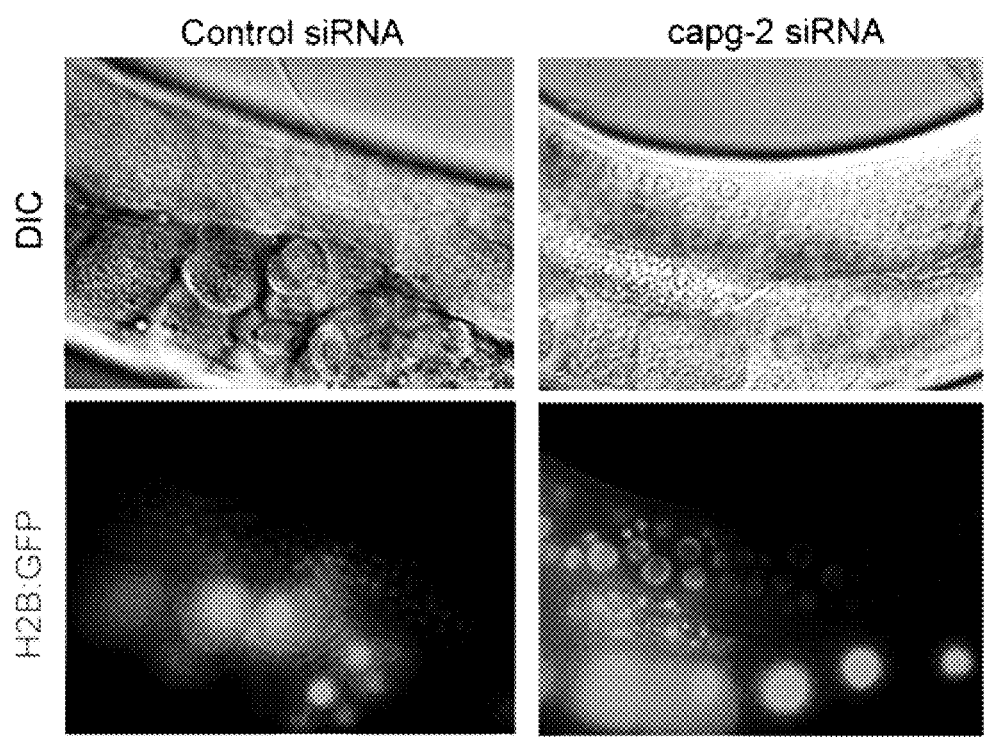
FIGS. 1A to 1E illustrate chromosomal segregation defects resulting from depletion of capg-2, Condensin II subunit of C. elegans.
Figure 1B:
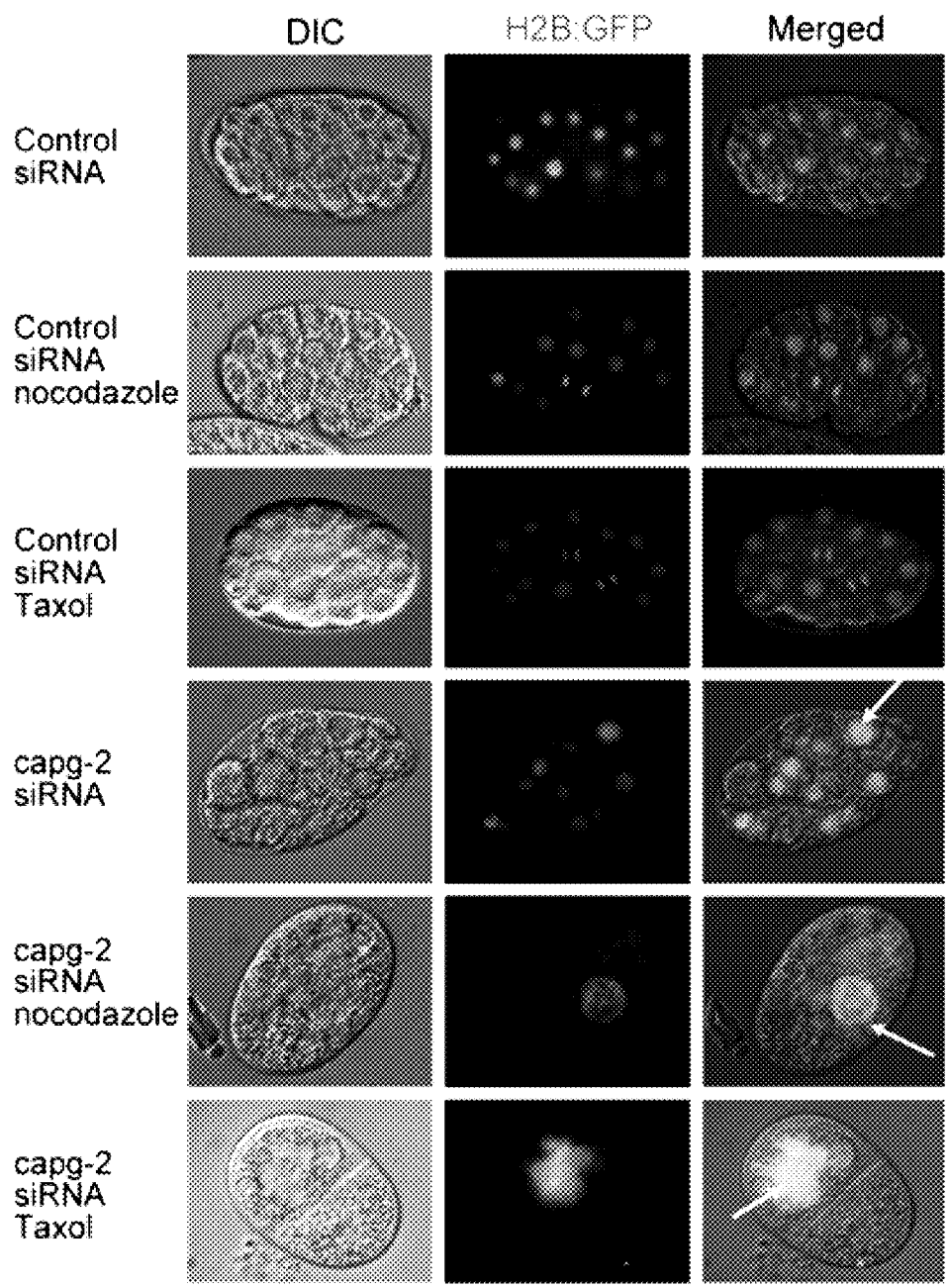
Figure 1C:
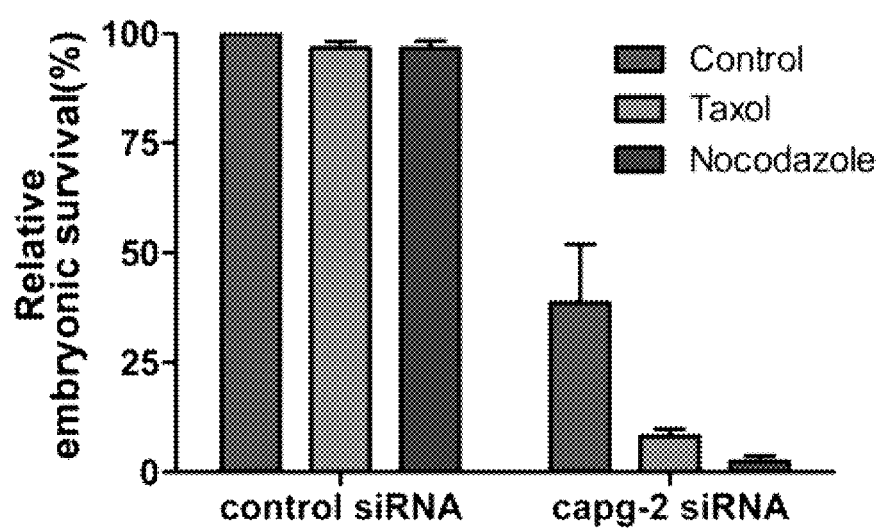
Figure 1D:
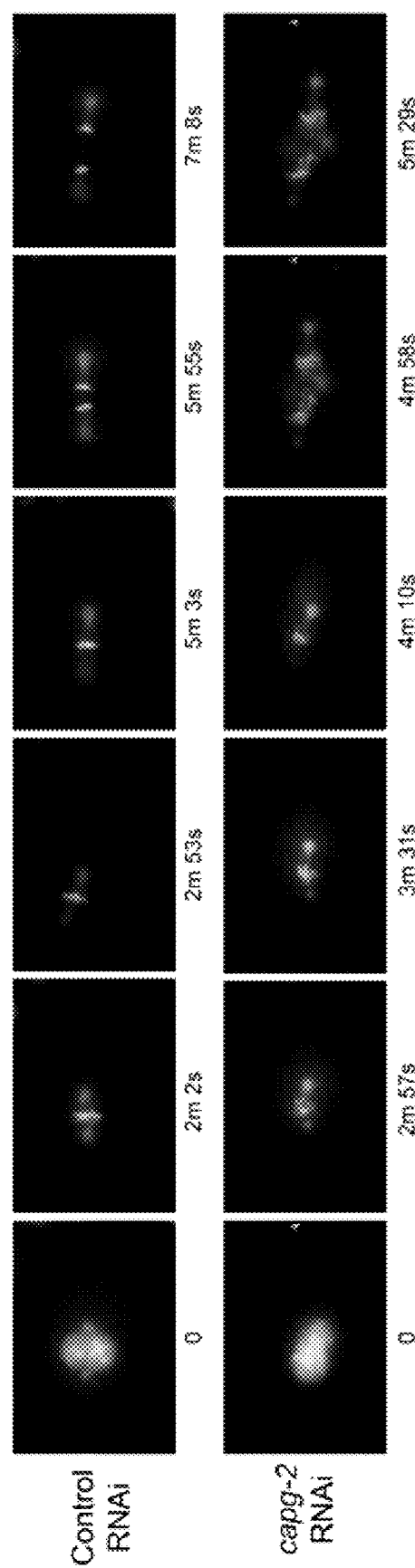
Figure 1E:
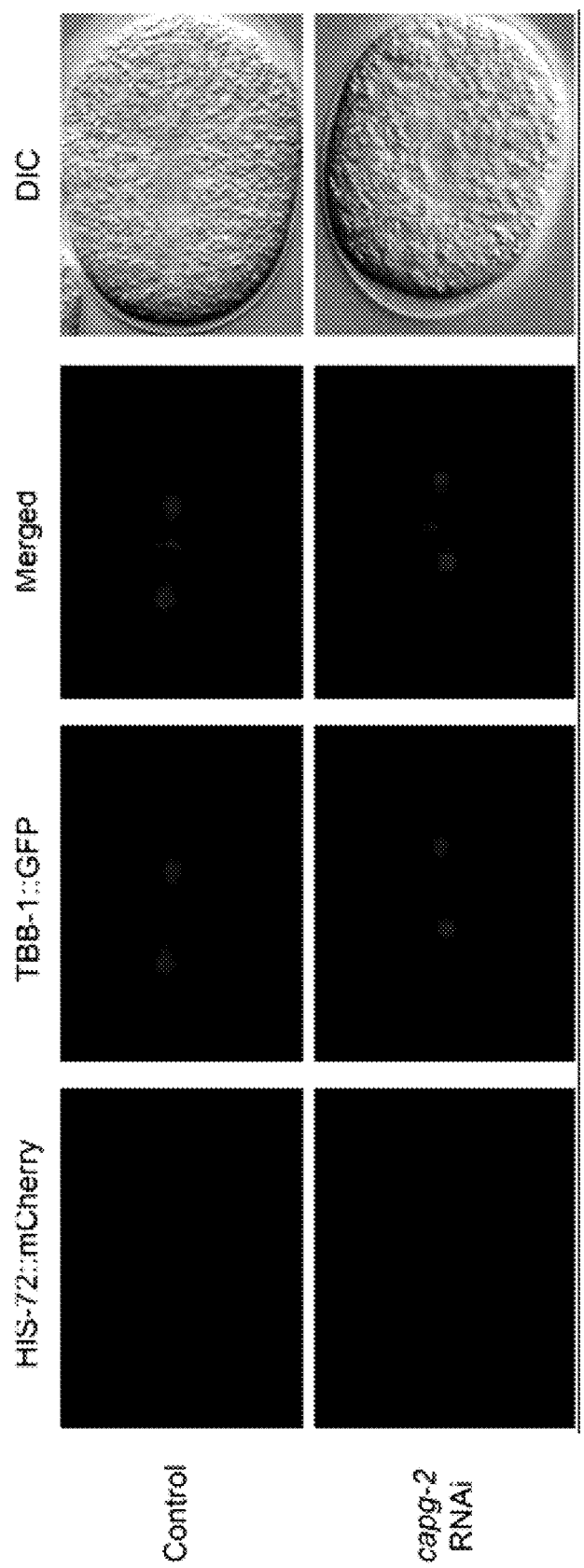
Figure 6A:
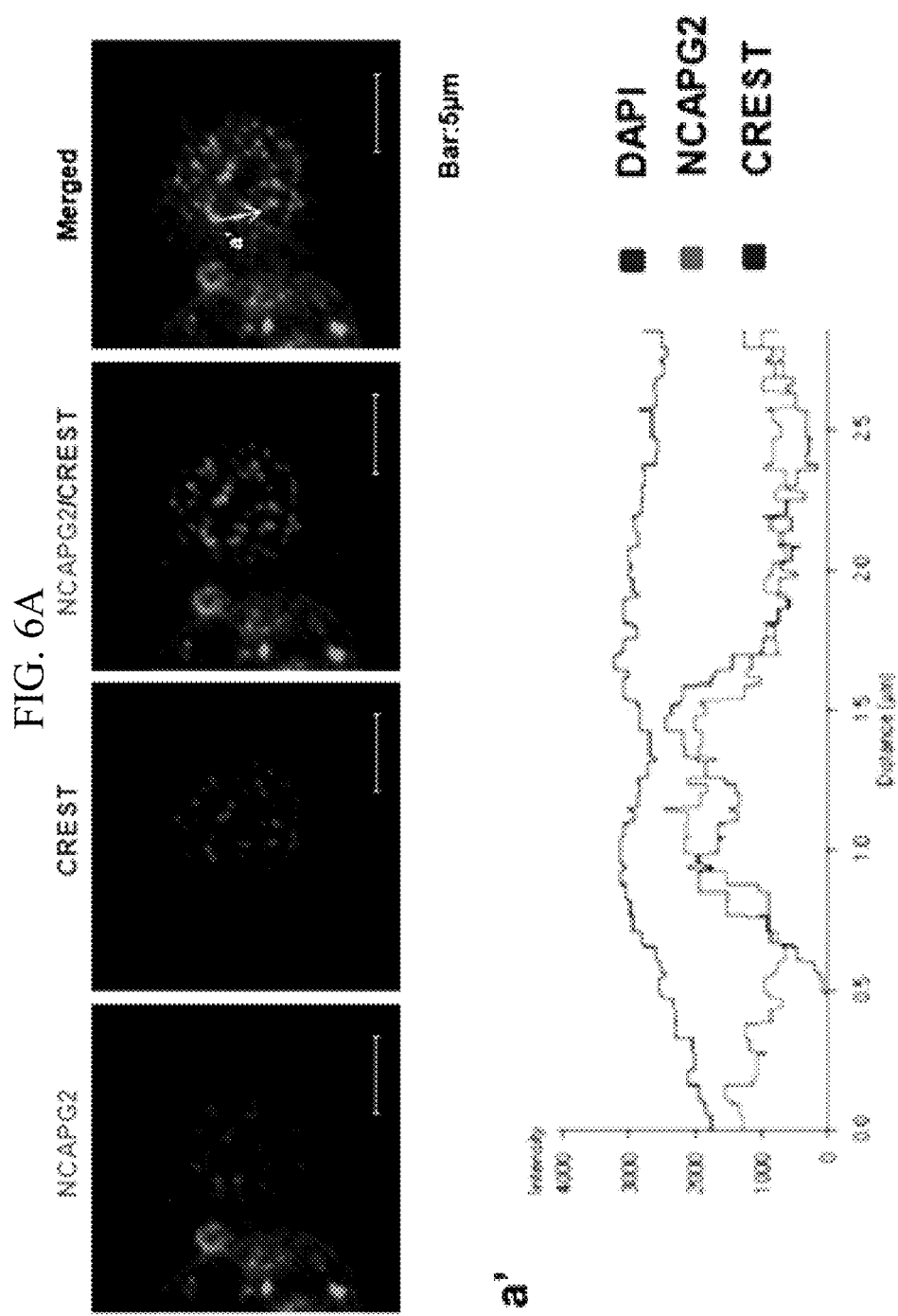

To investigate the role of NCAPG2 in chromosome segregation, we used *C. elegans* and human cells as model systems (FIGS. 1A to 1E and FIGS. 2A to 2C). When CAPG-2 was depleted in *C. elegans*, chromosome condensation occurred normally during early mitosis; however, chromosome alignment at the metaphase plate was delayed, and the chromosome was replicated again without cytokinesis (FIG. 1D). Interestingly, abnormal chromosome alignment by treatment with capg-2 feeding RNAi was caused by a dispersed orientation of the microtubule attachment (FIG. 1E). CAPG-2 depletion caused defects in the proper interaction between microtubules and the kinetochore during early mitosis, resulting in chromosome missegregation. However, these types of defects resulting from CAPG-2 depletion did not occur when other condensin components were depleted in *C. elegans*. Depletion of the condensin I complex component CAPG-1 occurs in the *C. elegans* chromosome segregation defect caused by Aurora B$^{AIR2}$-dependent chromosome obstruction (Bembenek, et al. Condensin and the Spindle Midzone Prevent Cytokinesis Failure Induced by Chromatin Bridges in *C. elegans* Embryos. *Curr Biol* 23, 937-946 (2013)). CAPG-1 depletion results in cytokinesis failure, which is characterised by anaphase bridge formation. Moreover, a temperature-sensitive mutant of another component of the condensin II complex, HCP-6 (NCAPD3 homologue in *C. elegans*), also shows chromosome segregation defects. However, this non-functional hcp-6 mutant shows merotelic kinetochore-microtubule interactions caused by a failure to maintain chromosome rigidity. The kinetochore-microtubule interaction defects observed in *C. elegans* are also observed in human cells (FIGS. 1A to 1E and FIGS. 2A to 2C). Consistent with previous observations, siRNA-mediated depletion of condensin II components in HeLa cells causes defects in chromosome segregation (Ono, T., et al. Spatial and temporal regulation of Condensins I and II in mitotic chromosome assembly in human cells. *Mol Biol Cell* 15, 3296-308 (2004)). NCAPD3 also plays a role in PLK1 localization to the chromosomal axes. These results suggest that two individual condensin II components independently recruit PLK1 to different chromosome regions. These NCAPD3 effects on PLK1 during mitosis could explain our observation that the NCAPG2 T1010A mutant still had weak binding to PLK1, although the NCAPG2-PBD interaction was completely abolished when NCAPG2 was unphosphorylated at Thr1010, suggesting indirect binding through the condensin II complex (FIGS. 6A and 6B). Condensin II complex localization at the centromere and at the chromosome arm is important for chromosome function during mitosis. Mitotic chromosome condensation, which is governed by condensin complex proteins, is necessary for the proper centromere structure for kinetochore complex assembly. NCAPG2 also has an additional role in proper microtubule attachment to the kinetochore via PLK1 for proper chromosome segregation.

Other proteins may be involved in PLK1 localization and delocalization to the kinetochore; PBIP1, BUB1, NUDC, INCENP and CUL3-KLHL22 may contribute co-operatively with or independent of NCAPG2. However, considering the depletion phenotypes, NCAPG2 plays the most critical role in the kinetochore-microtubule interaction governed by PLK1 during prometaphase to metaphase. Taken together, NCAPG2 contributes to PLK1 kinetochore localization for the kinetochore-microtubule interaction, and CUL3-KLHL22 delocalises PLK1 from the kinetochore after BubR1 phosphorylation. These results suggest that PLK1 localization to the kinetochore is governed by different proteins and depends on the timeline of mitosis progression. NCAPG2-regulated PLK1 localization occurs during the initial stage of the microtubule-kinetochore interaction because the NCAPG2 and PLK1 interactions primarily occur during prometaphase, before chromosome alignment is completed.

Figure 8A:
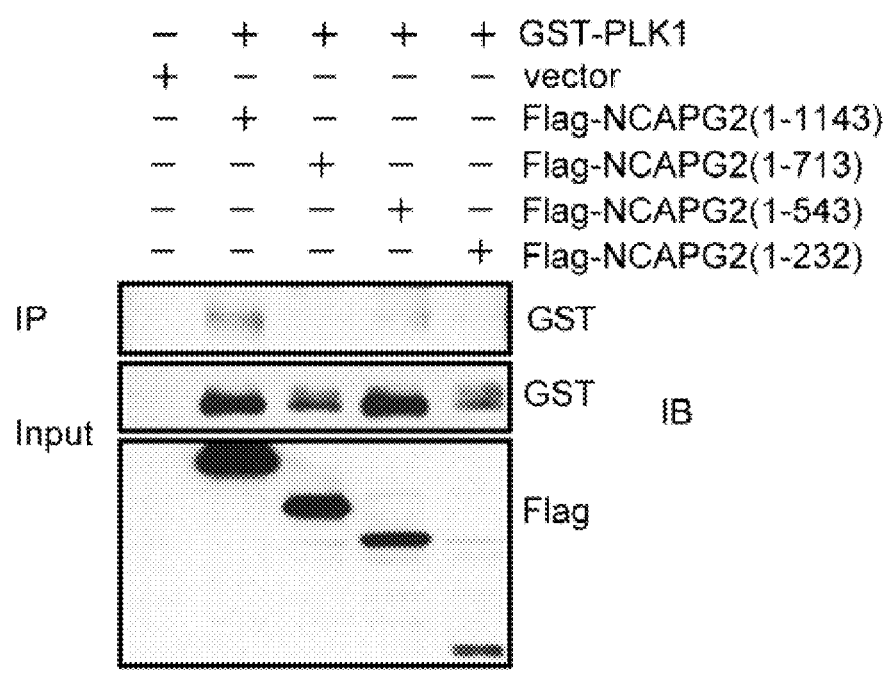
FIGS. 8A to 8F illustrate 1010T and 805T of NCAPG2 is a critical binding motif for PBD domain of PLK1.
Figure 8B:
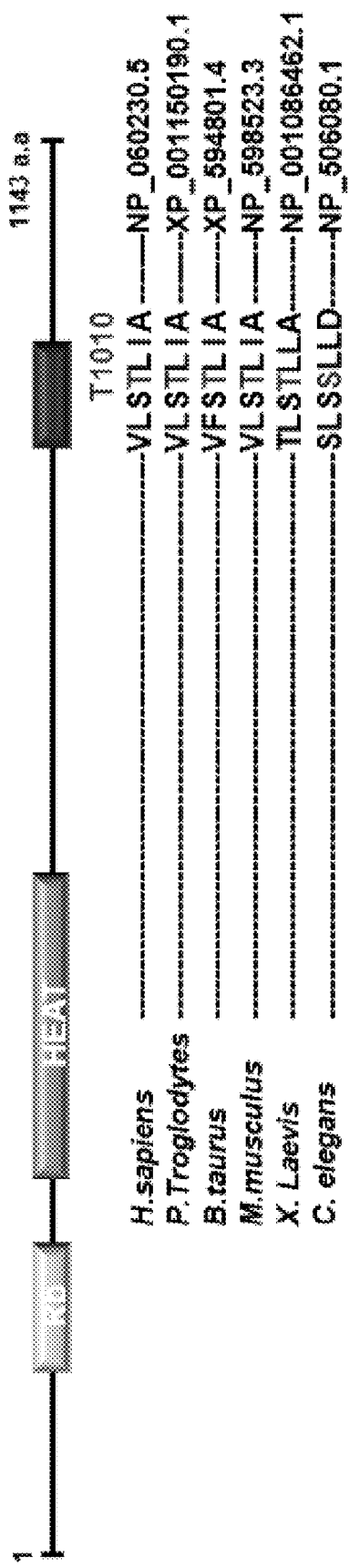
Figure 8C:
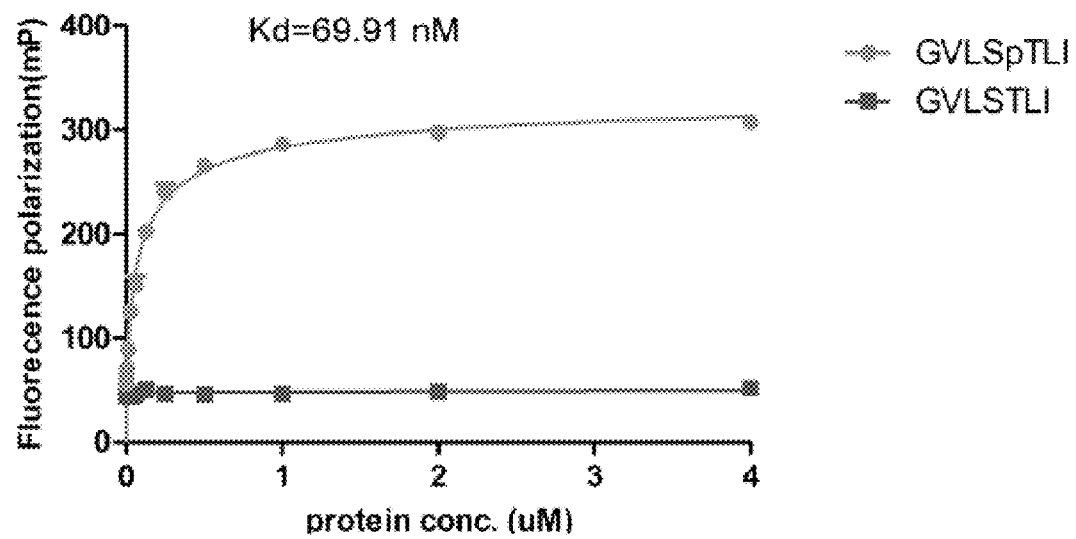

In addition, our results showed that NCAPG2 is critical for PLK1 kinetochore localization in both human and nematode cells (FIG. 3C and FIGS. 5, 6C to 6F), suggesting functional conservation of NCAPG2 in nematodes and vertebrates. Therefore, we hypothesised that the PBD-binding site may be conserved across species and found a conserved PBD-recognition region at the C-terminus of NCAPG2 (FIG. 8B). In human NCAPG2, the PBD-recognition region was 1007VLSpTLI1012, and *C. elegans* contained a similar sequence, 995SLSpSLL1000. The peptide in *C. elegans* is relatively conserved within −2 to +2 amino acid position with the human peptide; however, the threonine is replaced with serine. This region is highly conserved in other species, including *P. troglodytes* and *X. laevis*, indicating that the role of NCAPG2 in PLK1 localization to the kinetochore may be conserved (FIG. 8B). Our immunoprecipitation and in vitro binding assay data indicated that NCAPG2 and PLK1 directly interact with each other in a phosphorylation-dependent manner at Thr1010 (FIGS. 8B and 8C). We confirmed that Thr1010 could be phosphorylated during mitosis by using a phosphospecific antibody. In the present invention, we also determined the crystal structure of PLK1-PBD in complex with NCAPG2 phosphopeptides. This structure provides a detailed view of the interactions between PLK1 and NCAPG2. Additionally, our structure provides another opportunity for developing PLK1 inhibitors that target the PBD. Many extensive studies have been established to develop PLK1 inhibitors that target the PBD. These studies were initiated from structural investigations of the PBD and PBIP peptide structures. Because the peptide sequence from NCAPG2 is quite different from PBIP peptides, except for the characteristic S-pT residues, our structure will lay the groundwork for further developing PLK1 inhibitors.

Figure 10A:
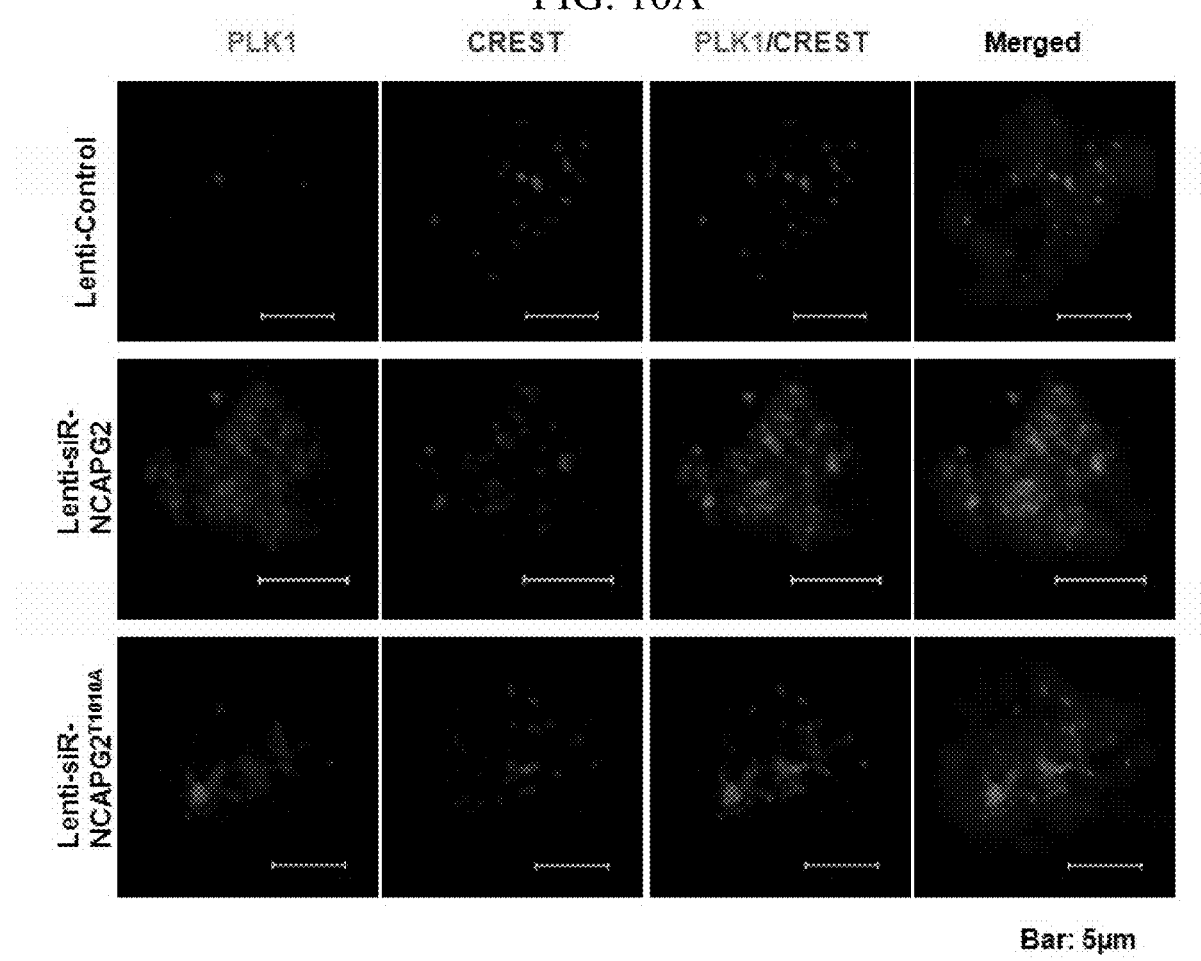
FIGS. 10A to 10C illustrate NCAPG2 T1010 is required for PLK1 recruiting to kinetochore.
Figure 10B:
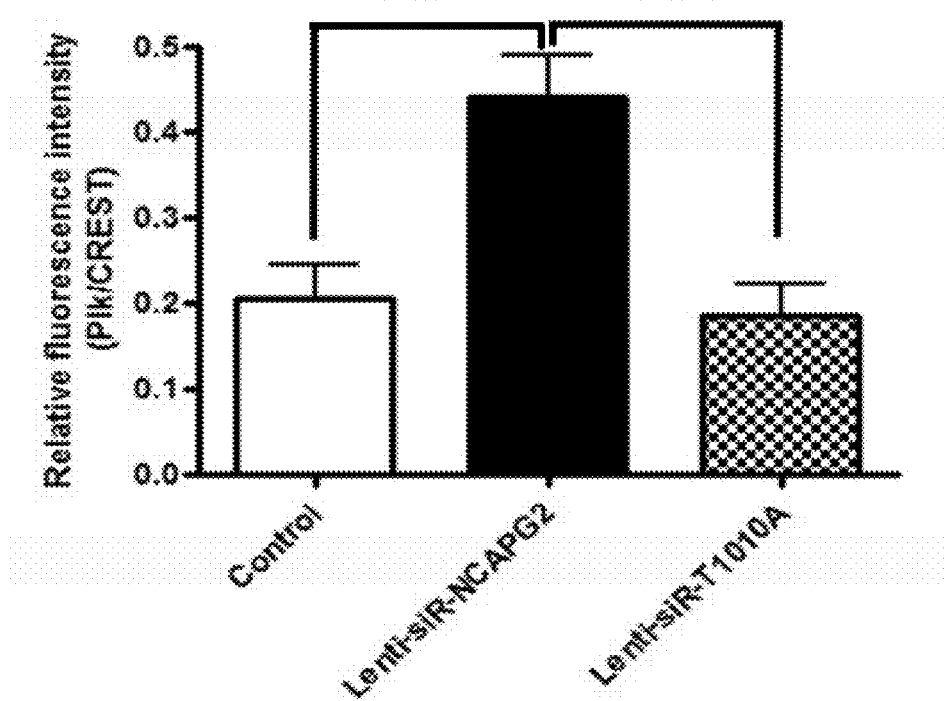
Figure 10C:
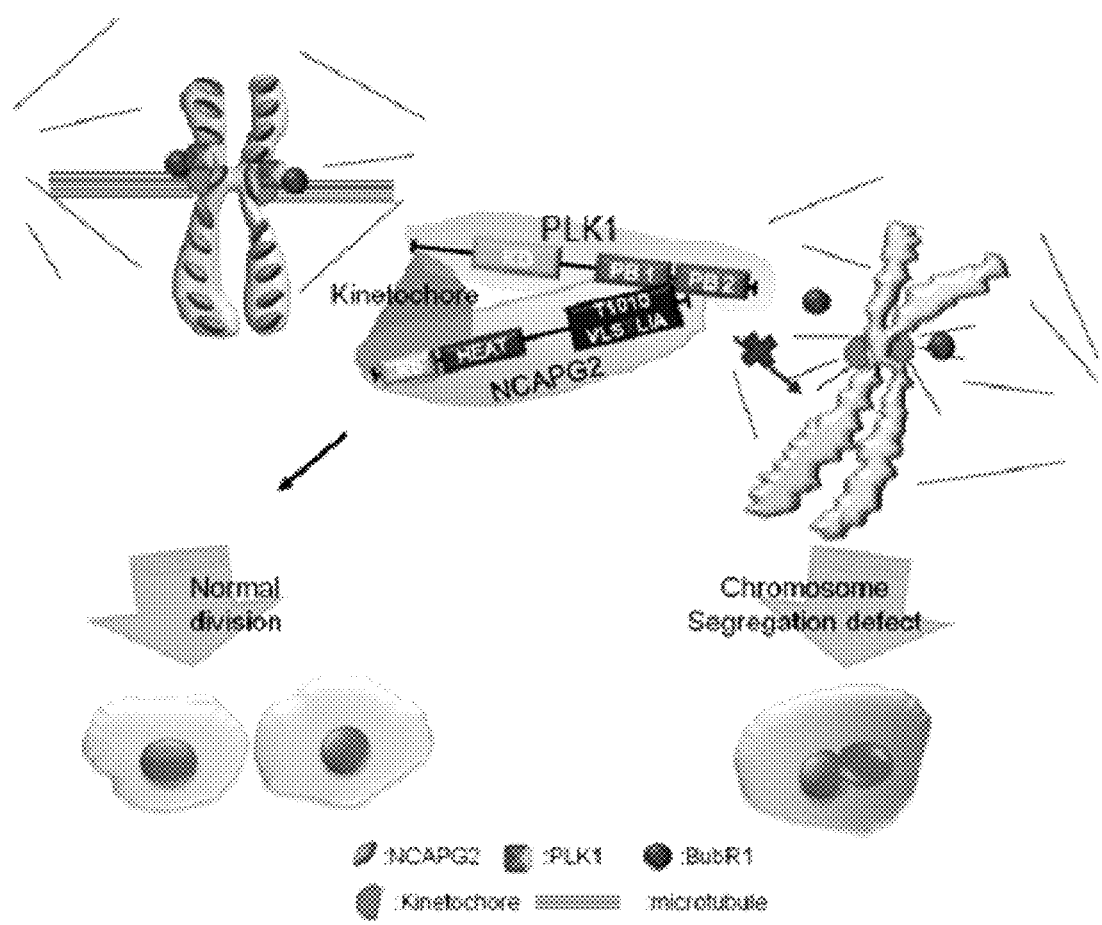

In summary, we found that NCAPG2 is a new critical player in PLK1 kinetochore localization. NCAPG2 interacts with PLK1 during the prometaphase-metaphase transition in unstable microtubule-kinetochore interactions. We suggest a model of NCAPG2 and PLK1 binding at the kinetochore for proper microtubule-kinetochore assembly (FIG. 10C). NCAPG2 localization and PLK1 recruitment to the kinetochores of misaligned chromosomes are critical for the completion of proper chromosome alignment at the metaphase plate. Our study suggests that the conserved function of NCAPG2 is essential for PLK1 localization to kinetochores and for proper chromosome segregation.

Therefore the present invention provides a protein mutant comprising an amino acid sequence having a substitution mutant on position 1010 of the amino acid sequence of SEQ ID NO: 7, a polynucleotide encoding the protein mutant, or a recombinant vector comprising the polynucleotide. In the protein mutant according to the present invention, the substitution mutant is, but is not limited to, threonine to alanine. Since the binding of the protein mutant to PLK1 is inhibited, the protein mutant according to the present invention can show anti-tumor activity.

Figure 12:
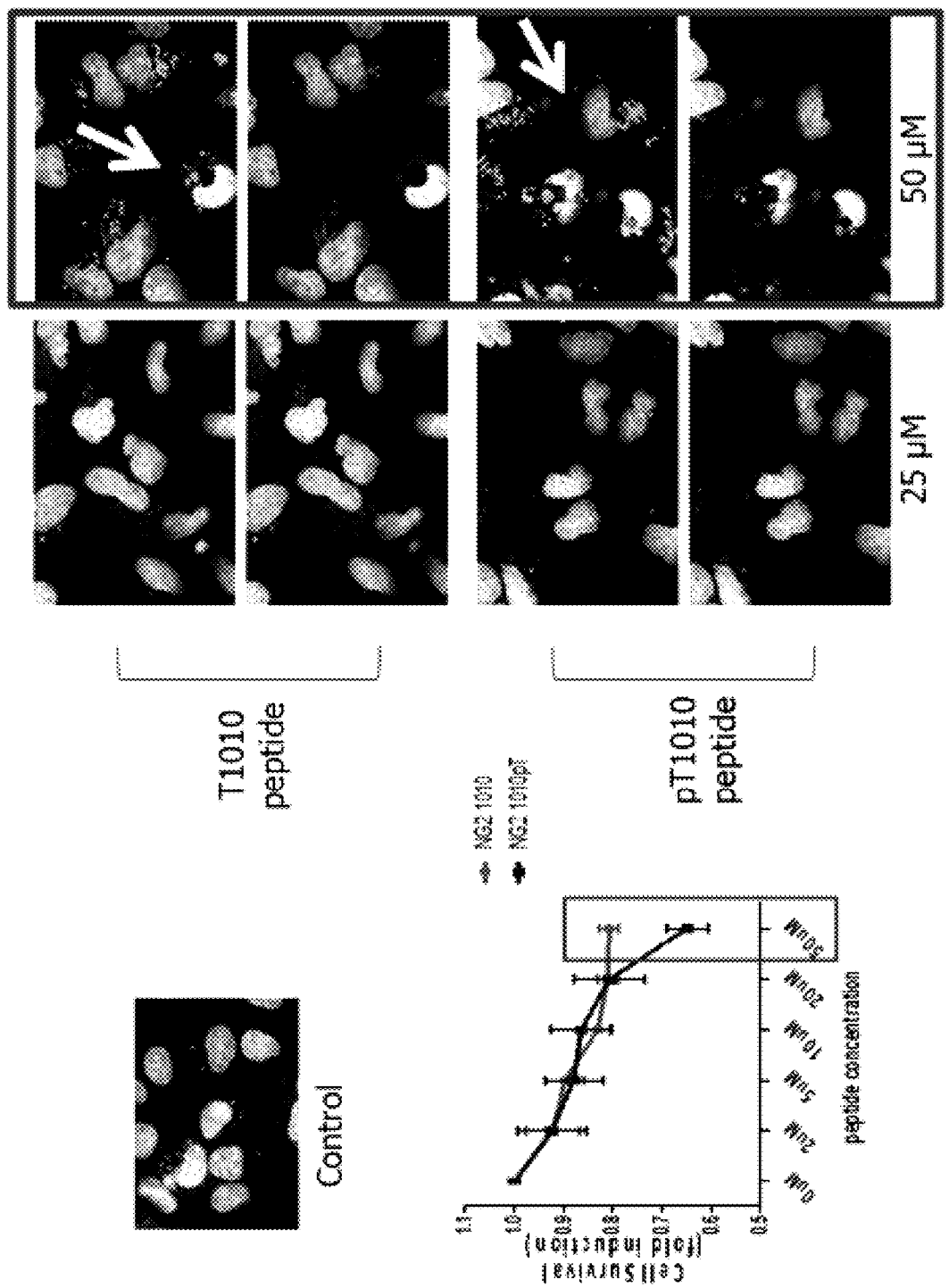
FIG. 12 illustrates NCAPG2 pThe1010 (VLSpTL) and NCAPG2 T1010 (VLSTL) peptide decreased cell survival and induced mitotic defect in HuR-7 human hepatoma cell. Cell survival and nucleus morphology were detected from Opera Phenix system (PerkinElmer).

Therefore the present invention provides NCAPG2 protein, mutant thereof, or peptides which can be used as a pharmaceutical composition or a novel target for treating disorders or disease caused by abnormal cell division including cancer. In one embodiment, we showed that NCAPG2 can inhibit proliferation of tumor cells by preventing PLK1 functioning in mitosis using NCAPG2-PLK1 binding (FIG. 12).

Thus, the present invention provides a pharmaceutical composition including anti-tumor agent, comprising NCAPG2 protein, a peptide comprised of a fragment of the NCAPG2 protein, or a polynucleotide encoding the protein or peptide. In one embodiment, the fragment comprises, but is not limited to, the amino acid residue number 805 or 1010 of SEQ ID NO: 7, or the sequence of SEQ ID NO: 8 or the sequence of SEQ ID NO: 11. There is no limit to the sequence of the polynucleotide if it can express the NCAPG2 protein or the peptide.

Figure 8D:
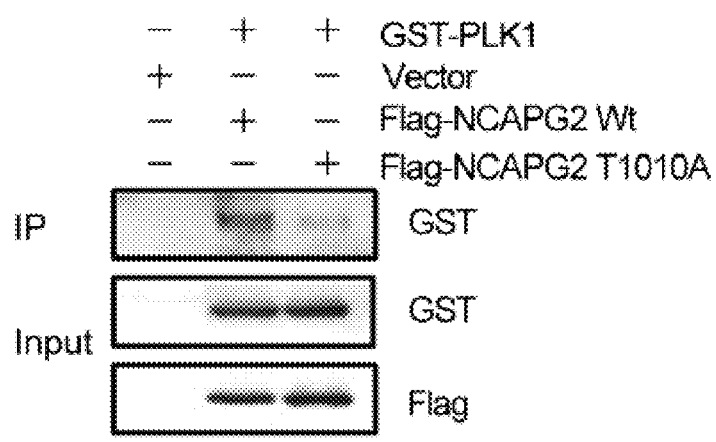
Figure 8E:
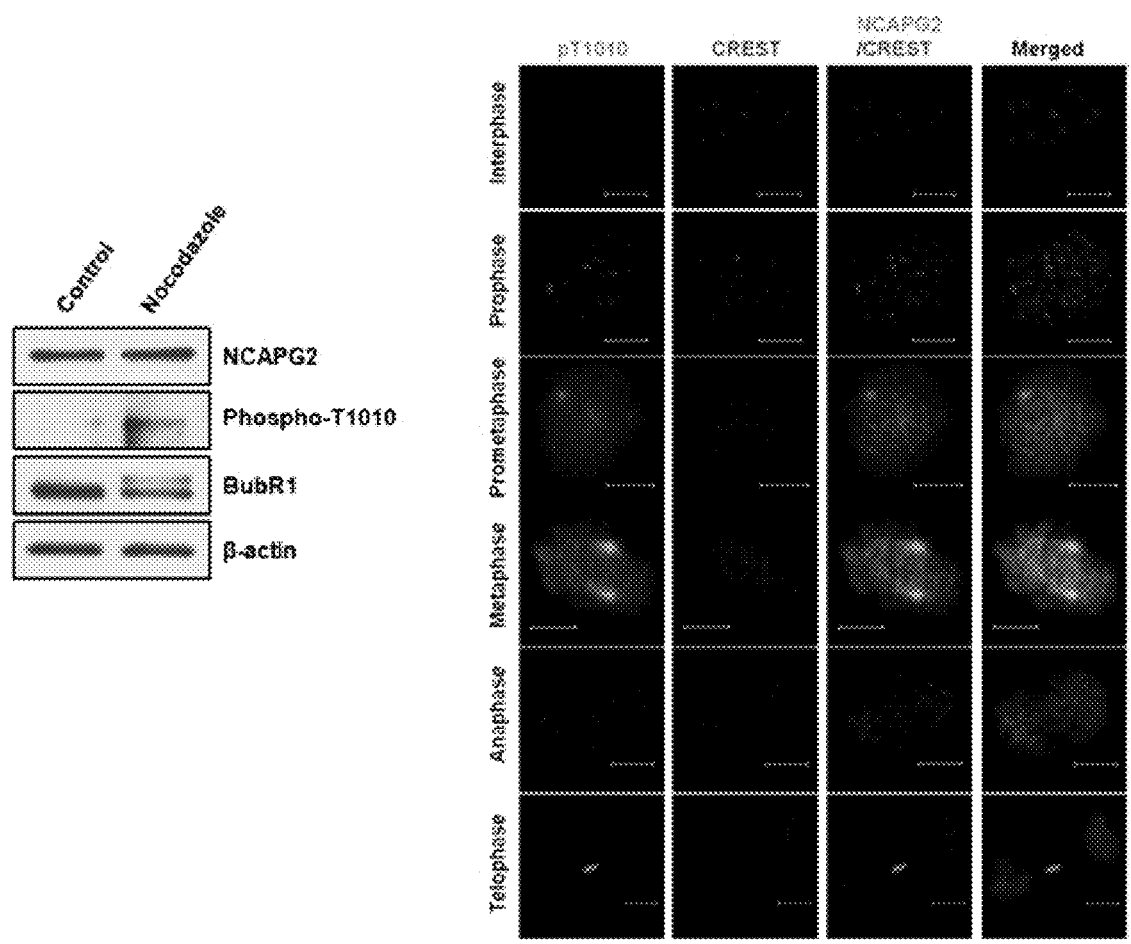

In another aspect, the present invention provides a pharmaceutical composition comprising a suppressor (or inhibitor) suppressing expression or activity of the NCAPG2 protein, peptide, or the polynucleotide since NCAPG2 makes PLK1 function normally in mitosis through NCAPG2-PLK1 binding. In one embodiment, the suppressor comprises a single organic compound, a single inorganic compound, a biopolymer including peptide, protein, nucleic acid or lipid, or a complex compound. The suppressor can be manufactured according to known methods by a person having ordinary skill in the art. In one embodiment, the suppressor comprises a mutator nucleotide sequence that mutates the amino acid residue 805 or 1010 of SEQ ID NO: 7. In one embodiment, the mutator nucleotide sequence that mutates the amino acid residue 1010 of SEQ ID NO: 7 comprises, but is not limited to, a primer of SEQ ID NO: 5 or SEQ ID NO: 6. In one embodiment, the mutator nucleotide sequence that mutates the amino acid residue 805 of SEQ ID NO: 7 comprises, but is not limited to, a primer of SEQ ID NO: 9 or SEQ ID NO: 10. In another embodiment, the suppressor comprises an inhibitor that suppresses the phosphorylation of amino acid residue 1010 of SEQ ID NO:

7 (Thr1010) since the phosphorylated 7-mer peptide $^{1006}$GVLS-pT-LI$^{1012}$ interacts strongly with PBD of PLK1 in contrast to the unphosphorylated peptide $^{1006}$GVL-STLI$^{1012}$ (SEQ ID NO: 8) (FIG. 8C), and the phosphorylation of amino acid residue 1010 of SEQ ID NO: 7 has a critical role in NCAPG2 or PLK1 function (FIG. 8E). The phosphorylation inhibitor can show anti-tumor activity by suppressing the activity of PLK1 by inhibiting the interaction between NCAPG2 and PLK1. In one embodiment, the inhibitor comprises, but is not limited to, a mutator nucleotide sequence that mutates the amino acid residue 1010 of SEQ ID NO: 7. The mutator nucleotide sequence comprises, but is not limited to, a primer of SEQ ID NO: 5 or SEQ ID NO: 6.

In one embodiment, the pharmaceutical composition according to the present invention can be used for anti-cancer treatment, wherein the tumor refers to all types of cancers or neoplasm or malignant tumors found in mammals, including tumors and leukemia, for example, but is not limited to, breast cancer, bladder cancer, colon cancer, melanoma, liver cancer, lung cancer, gastric cancer, esophageal cancer, prostate cancer, leukemia, etc. The active ingredients of the present invention (e.g., a NCAPG2 peptide or suppressor) can be administered alone or as a pharmaceutical composition, thus the invention further provides pharmaceutical compositions and methods of making said pharmaceutical composition. In one embodiment, the pharmaceutical composition comprises an effective amount of NCAPG2 peptide or NCAPG2 suppressor. The pharmaceutical composition may comprise of admixing at least one active ingredient, or a pharmaceutically acceptable salt, prodrug, solvate, polymorph, tautomer or isomer thereof, together with one or more carriers, excipients, buffers, adjuvants, stabilizers, or other materials well known to those skilled in the art and optionally other therapeutic agents such as microtubule inhibitors, taxol, nocodazole, kinesin inhibitor, etc. The formulations may conveniently be presented in unit dosage form and may be prepared by any methods well known in the art of pharmacy. Some embodiments relate to a pharmaceutical composition with a combination of the active ingredient and a pharmaceutically acceptable carrier. The pharmaceutically acceptable carriers include, but are not limited to, water, salt solutions, alcohols, gum arabic, vegetable oils (e.g., almond oil, corn oil, cottonseed oil or peanut oil), glyceride, carbohydrates (e.g., lactose, amylose or starch), magnesium stearate, talc, silicic acid, viscous paraffin, fatty acid monoglycerides and diglycerides, pentaerythritol fatty acid esters, hydroxy methylcellulose, polyvinyl pyrrolidone, aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of excipients that may be used in conjunction with the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described in the following references: 7 Modern Pharmaceutics, Chapters 9 and 10 (Banker & Rhodes, Editors, 1979); Lieberman et al., Pharmaceutical Dosage Forms: Tablets (1981); and Ansel, Introduction to Pharmaceutical Dosage Forms 2nd Edition (1976).

The pharmaceutical composition of the invention is suitable to be administered as a cancer therapy to any mammal, including human beings. Any suitable dosage may be given in the method of the invention. The type of compounds and the carriers and the amount will vary widely depending on the species of the warm blooded animal or human, body weight, and cancer, or tumor being treated. The range and ratio of the chemotherapeutic agent and anti cancer compound used will depend on the type of chemotherapeutic agent and the cancer being treated. Generally, the dosage in man is lower than for small warm blooded mammals such as mice. A dosage unit may comprise a single compound or mixtures thereof with other compounds or other cancer inhibiting compounds. The dosage unit can also comprise diluents, extenders, carriers and the like. The unit may be in solid or gel form such as pills, tablets, capsules, liposomes and the like or in liquid form suitable for oral, rectal, topical, intravenous injection or parenteral administration or injection into or around the tumor or into or around the bone marrow. The anti-cancer compounds and chemotherapeutic agents are typically mixed with a pharmaceutically acceptable carrier. This carrier can be a solid or liquid or a liposome and the type is generally chosen based on the type of administration being used. The active agent can be coadministered in the form of a tablet or capsule, liposome, or as an agglomerated powder or in a liquid form.

The pharmaceutical composition can be used for any suitable method which is effective in the treatment of the particular cancer or tumor type that is being treated. Treatment may be oral, rectal, topical, parenteral or intravenous administration or by injection into the tumor and the like. The method of applying an effective amount also varies depending on the tumor being treated. It is believed that parenteral treatment by intravenous, subcutaneous, or intramuscular application of the benzimodale compounds, formulated with an appropriate carrier, additional cancer inhibiting compound or compounds or diluent to facilitate application will be the preferred method of administering the compounds to warm blooded animals.

In another aspect, the present invention provides a method for screening a novel anti-tumor agent since the NCAPG2 protein or peptide can be related to anti-tumor activity through the interaction with PLK1. In one embodiment, the method comprises, preparing a cell or an animal expressing NCAPG2 protein or a peptide derived from the NCAPG2 protein; treating the cell or the animal with a substance specifically interacted with the protein, the peptide or a polynucleotide encoding the protein or the peptide; and determining whether the protein or the peptide binds to PLK1 (polo-like kinase 1). The method further comprises detecting phosphorylated threonine on position 1010 of the amino acid sequence.

Since the normal function of PLK1 induced by NCAPG2-PLK1 binding is essential for mitosis of cancer cell, the substance blocking the interaction between NCAPG2 and PLK1 can be an effective anti-tumor agent. In one embodiment, the peptide comprising a fragment of NCAPG2 protein having the amino acid sequence of SEQ ID NO: 7. In one embodiment, the fragment comprises the amino acid residue number 805 or 1010 of SEQ ID NO: 7, or the sequence of SEQ ID NO:8 or SEQ ID NO: 11. In one embodiment, the cell comprises an expression vector comprising a nucleotide sequence encoding the NCAPG2 protein or peptide. The cell can express the peptide temporarily or consistently by the transfected or infected expression vector. The expression vector can be made by a method for constructing recombinant DNA well known in the art. For example, the expression vector comprises, but is not limited to, plasmid, lentiviral vector, retroviral vector and adenoviral vector which are used for replication or expression in target cells including mammalian cell.

The substance specifically interacted with the protein, peptide or a polynucleotide encoding the protein or peptide comprises any substance inhibiting the expression or activity of the protein, peptide or polynucleotide. In one embodiment, the substance may be selected from a single organic compound, a single inorganic compound, a biopolymer including peptide, protein, nucleic acid or lipid, or a complex compound. For example, siRNA, antisense oligonucleotide, ribozyme, antibody, aptamer, spiegelmer, or a combination thereof may be used as the substance.

Well known standard techniques can be used for determining whether the protein or the peptide binds to PLK1. For example, RT-PCR, qRT-PCR, western blot or fluorescent tags may be used as standard analysis method for detecting protein expression, and in vitro pull down assay, immunoprecipitation method or fluorescence polarization assay may be used to detect the interaction between NCAPG2 and PLK1.

EXAMPLES

The following examples are given to illustrate the present invention. It should be understood, however, that the invention is not to be limited to the specific conditions or details described in these examples.

Example 1

C. elegans Strains and RNA Interference

C. elegans were cultivated on NGM plates at 20° C. as a standard culture method (Brenner, S. *Genetics* 77, 71-94 (1974)). The capg-2 RNAi clone was obtained from Dr. J. Ahringer's bacteria-feeding RNAi library, which was a kind gift from Dr. J. Lee (Seoul National University). The wild-type N2 strain was used for measuring embryo lethality when capg-2 RNAi was treated with nocodazole. RW10006 (HIS-72::GFP), XA3501 (GFP::HIS-11 and GFP::TBB-2), JG479 (NPP-1::GFP, mCherry::HIS-58 and GFP::TBB-2) and SA127 (GFP::PLK-1) were used to determine the effects of capg-2 knockdown on mitosis. JG479 was generated by crossing XA3501 and OCF3 (NPP-1::GFP and mCherry::HIS-58). HIS-72 is histone 3, and TBB-2 is β-tubulin. Both HIS-11 and HIS-58 are histone 2B proteins (www.wormbase.org). Most strains were provided by the CGC, which is funded by the NIH Office of Research Infrastructure Programs (P40 OD010440). For capg-2 RNA interference, L4 worms were transferred to the RNAi plate, and the F1 embryos were observed. The HT115 E. coli strain, which contains the empty RNAi vector (L4440), was used as the control. To compare the survival ratios of embryos when capg-2 RNAi was treated with or without nocodazole, L4 worms were grown in liquid with or without nocodazole for 12 hours after feeding on the capg-2 RNAi or control plates for 12 hours. Next, the worms were recovered on NGM plates, and 3 adult worms were transferred to NGM plates. The worms were removed after laying eggs for 12 hours, and the dead embryos were counted the next day. We examined 3 plates for each case, and all repeated tests showed the same tendency 3 times. The liquid culture used in the 96-well plates contained *E. coli* (OP50) and cholesterol, and the culture volumes were 100 µl each of nocodazole (20 µg ml$^{-1}$) and 1% DMSO (control). All images of *C. elegans* embryos were observed and captured using an Imager A2 compound microscope (Carl Zeiss) or an LSM700 confocal microscope (Carl Zeiss).

Example 2

Experimental Conditions

MDA-MB-231 and HEK293 cells, which were purchased from the American Type Culture Collection (ATCC), were grown in Dulbecco's modified Eagle's media (DMEM; Invitrogen) supplemented with 10% FBS (Invitrogen) and 1% penicillin-streptomycin (P/S) in a 5% $CO_2$ atmosphere at 37° C. Small interfering RNAs (siRNAs) for NCAPG2 were synthesised using 5'-GCU UCA UAG GGU CAU UUA UTT-3' (SEQ ID NO: 1) and 5'-GAA GAA UGA UGC UGA AAC ATT-3' (SEQ ID NO: 2) sequences (ST Pharm. Co. LTD). Expression vectors or siRNAs were transferred into the cells using the Amaxa Nucleofector system (Amaxa Biosystems) according to the manufacturer's instructions. For synchronising cells into a specific phase, 50 ng ml$^{-1}$ nocodazole (Sigma-Aldrich) or 100 µM monastrol (Sigma-Aldrich) was used.

Example 3

Immunofluorescence Imaging

Cell were grown on coverslips, rinsed twice with PHEM buffer (60 mM PIPES, 25 mM HEPES, 10 mM EGTA, and 2 mM $MgCl_2$, pH 6.9 with KOH), permeabilised with 0.5% Triton X-100 in PHEM buffer at 4° C. for 1 min, and fixed with 4% paraformaldehyde in PHEM buffer. The fixed cells were incubated at 4° C. for 1 hr with each primary antibody, followed by incubation with a secondary antibody plus 100 ng ml$^{-1}$ DAPI for 3 hr. The acquired images were analysed using a confocal microscope (Zeiss 510 Meta, Carl Zeiss). Live cell imaging was detected every 15 sec for 72 hr, 0.5 sec exposures were acquired using 2×NA0.75 objective on an LSM500 META Confocal Microscope (Carl Zeiss).

Example 4

Counting the Chromosome Number

Cells were harvested after 4 hr colcemid (0.1 µg ml$^{-1}$) treatment with or without nocodazole (50 ng ml$^{-1}$) pretreatment. The harvested cells were incubated with a hypertonic solution (0.075 M KCl) and with freshly prepared fixative (methanol/acetic acid, 3:1). The swollen cells were spread onto a glass slide. The slides were dried at room temperature, stained with DAPI (100 ng ml$^{-1}$), and visualised under a confocal microscope.

Example 5

Vector Construction and Site-Directed Mutagenesis

The NCAPG2 expression vectors were constructed using pcDNA3.1, pCMV-3FLAG-1, and pLL3.7 vectors with KpnI/XhoI, EcoRV/XhoI, and SmaI/XhoI restriction enzyme sites, respectively. To produce siRNA-resistant NCAPG2 mutants (Lenti-NCAPG2$^R$), the mutants (forward primer: 5' GAA GAC TAC CTG AAG CTT CACAGAGTG ATT TAT CAG CAA ATT ATC CAG ACC TAC CTG-3' (SEQ ID NO: 3), reverse primer: 5'-CAG GTA GGT CTG GAT AAT TTG CTG ATA AAT CACTCTGTG AAG CTT CAG GTA GTC TTC TTC-3' (SEQ ID NO: 4)) were generated using a QuikChange Site-Directed Mutagenesis Kit (Stratagene). To produce NCAPG2$^{T1010A}$, the mutations (NCAPG2$^{T1010A}$ forward primer: 5'-GGG GTG TAC TTT CTGCTC TGA TCG CTG G-3' (SEQ ID NO: 5), NCAPG2$^{T1010A}$ reverse primer: 5'-CCA GCG ATC AG AGCA GAA GAT ACA CCC C-3' (SEQ ID NO:6)) were generated using QuikChange II Site-Directed Mutagenesis Kit (Stratagene) into Flag-NCAPG2 or Lenti-siR-NCAPG2 vectors. To produce NCAPG2$^{T805A}$, the mutations (NCAPG2$^{T805A}$ forward primer: 5'-CAC TTC TGC AGA CGC CGG GTG GGA AG-3' (SEQ ID NO: 9), NCAPG2$^{T805A}$ reverse primer: 5'-CT TCC CAC CCG GCG TCT GCA GAA GTG-3' (SEQ ID NO: 10)) were generated using QuikChange II Site-Directed Mutagenesis Kit (Stratagene) into Flag-NCAPG2 vector. Flag-Plk1, Flag-Plk1 (1-400), Flag-Plk1 (400-603), and Flag-Plk1$^{FAA}$ vectors were prepared as previous described.

Example 6

Immunoprecipitation and Immunoblotting

For the immunoprecipitation experiment, cells were lysed with TAP buffer (25 mM Tris (pH 7.4), 140 mM NaCl, 0.5% NP-40, 10 mM NaF, 1 mM DTT, 1 mM PMSF, 1 mM EDTA, 1 mM Na$_3$VO$_4$, 1 mM β-glycerophosphate, 10% glycerol, and 0.2% protease inhibitor cocktail) and incubated with rabbit-IgG (Jackson Laboratory), anti-FLAG M2 affinity gel (Sigma-Aldrich), anti-NCAPG2 antibody or Glutathione Sepharose™ 4B (GST-beads, GE Healthcare Lunar, Madison, Wis.) at 4° C. The primary antibodies were purchased from commercial sources as follows: Histon H3 pS10 (Abcam, Cambridge, UK), NCAPG2 (Novus Biological, 1/1000), PLK1 (Novus Biological, 1/1000), BubR1 (BD Biosciences, 1/1000), β-actin (Sigma-Aldrich, 1/5000), and CREST (ImmunoVision, 1/1000). BubR1 676 antibodies (1/10000) were prepared as previously reported (Elowe, S., et al. Tension-sensitive Plk1 phosphorylation on BubR1 regulates the stability of kinetochore microtubule interactions. *Genes Dev* 21, 2205-19 (2007)). The precipitates were washed with TAP buffer three times at 4° C., re-suspended in 20 µl of 2$_X$ Sample buffer (125 mM Tris (pH 6.8), 200 mM DTT, 4% SDS, 20% Glycerol, 0.004% Bromophenol Blue) and proteins were denatured at 100° C. for 5 min.

For the detection of proteins using the immunoblottings, subjects were protein complexes from immunoprecipitation or whole cell lysates harvested from indicated conditions. Whole cells were harvested with lysis buffer (20 mM Tris, 5 mM EDTA, 10 mM Na$_4$P$_2$O$_7$, 100 mM NaF, 2 mM Na$_3$VO$_4$, 1% Np-40, 0.2% Protease Inhibitor Cocktail, and 1 mM PMSF) and centrifuged at 10,000 rpm, 4° C., 10 min. Protein concentration was determined using BCA™ protein assay kit (Pierce, Rockford, USA). Protein extracts were resuspended in 5$_X$ Sample buffer (50 mM Tris (pH 6.8), 100 mM DTT, 2% SDS, 0.1% Bromophenol Blue, and 10% glycerol), boiled for 5 min, and subjected to 8-12% SDS-polyacrylamide gel electrophoresis. Separated proteins were transferred into a Trans-Blot Nitrocellulose Membrane (Schleicher & Schuell, Keene, N.H., USA). Transferred membranes were blocked in 5% Skim milk in TBST buffer (10 mM Tris, pH 8.0, 150 mM NaCl, 0.05% Tween 20) and incubated with several primary antibodies. Protein expressions detected chemiluminescent signals activated by SuperSignal West Pico Chemiluminescent Substrate (Pierce Rockford, Ill., USA) reacted with horse radish peroxidase tagged secondary antibodies (Jackson ImmunoResearch Laboratories, Inc., West Grove, USA).

Example 7

Expression and Purification of PBD of PLK1

The human PLK1-PBD (371-594) was amplified by PCR and cloned into the pGEX6p-1 vector using the EcoRI and XhoI restriction enzyme sites. The protein was overexpressed in *E. coli* Rosetta2(DE3)pLysS cells (Novagen). The cells were grown at 37° C. in 3 L of Terrific Broth medium to an OD600 of 0.6, and recombinant protein expression was induced with 0.1 mM isopropyl β-D-thiogalactopyranoside (IPTG) at 20° C. The cells were further grown at 20° C. for 20 hr after IPTG induction. The purification methods were similar to methods that have been previously reported (Cheng, K. Y., et al. The crystal structure of the human polo-like kinase-1 polo box domain and its phospho-peptide complex. *EMBO J* 22, 5757-68 (2003)). Briefly, the cell pellet was resuspended in ice-cold HBS buffer (10 mM HEPES pH 7.5, 200 mM NaCl, 3.4 mM EDTA, 0.01% (v/v) 1-thioglycerol) and homogenized by sonication. After sonication, the cell debris was centrifuged and supernatant was applied to GST Sepharose resin (GE Healthcare). After extensive washing with HBS buffer, protein was eluted with HBS buffer supplemented with 20 mM reduced glutathione. PreScission protease (GE Healthcare) was added to eluted protein in order to remove the fused GST and the cleavage product was diluted and re-passed through GST Sepharose column. The flow through was collected and applied to Superdex 75 prep grade column (GE Healthcare) equilibrated with HBS buffer. The purified protein was concentrated to 6 mg/ml and used for fluorescence polarization binding assay or crystal screening.

Example 8

Crystallisation and Structure Determination

The purified PBD and 5-mer 1010pT peptide (Ac-VL-SpTL-NH$_2$; 5 mM final concentration) were mixed and stored on ice for an hour before the crystallisation trial. The crystals of the PLK1-PBD in complex with the 1010pT peptide were obtained using the sitting drop vapour diffusion method. Crystals were grown in a reservoir solution of 200 mM potassium iodide, 100 mM MES (pH 6.5), and 25% (v/v) PEG 4000. X-ray diffraction data were collected using an ADSC Q315r CCD detector at Pohang Light Source, Korea. Intensity data were processed and scaled using the program HKL2000 (Otwinowski, Z. & Minor, W. Processing of X-ray diffraction data collected in oscillation mode. in *Methods in Enzymology, Macromolecular Crystallograpy*, Vol. 276 (ed. C. W. Carter, J., and R. M. Sweet) 307-326 (Academic Press, New York, 1997)). The structure was determined by molecular replacement using the program Phaser (McCoy, A. J. Solving structures of protein complexes by molecular replacement with Phaser. *Acta Crystallogr D Biol Crystallogr* 63, 32-41 (2007)), and the model was refined using the program Phenix (Adams, P. D. et al. PHENIX: a comprehensive Python-based system for macromolecular structure solution. *Acta Crystallogr D Biol Crystallogr* 66, 213-21 (2010)). Manual model building was performed using the program Coot (Emsley, P. & Cowtan, K. Coot: model-building tools for molecular graphics. *Acta Crystallogr D Biol Crystallogr* 60, 2126-32 (2004)).

Example 9

Fluorescence Polarisation Binding Assay for the PBD

For the fluorescence polarisation binding assay, FITC-labelled 1010pT (GVLSpTLI) or 1010T (GVLSTLI) (SEQ ID NO: 8) peptide was mixed with purified PBD and incubated in a buffer containing 10 mM HEPES (pH7.5), 50 mM NaCl, 1 mM EDTA, 1 mM DTT, and 0.0025% (v/v) Tween 20. The final protein concentrations ranged from 0 to 4 µM, and the final peptide concentration was 10 nM. Fluorescence polarisation was analysed 30 min after mixing the peptide and proteins in a 96-well plate using a VERSA-max microplate reader (Molecular Devices). Binding curves were fitted using GraphPad Prism software (GraphPad Software).

Accession code. The coordinate for PBD of PLK1: 1010pT peptide complex has been deposited in Protein Data Bank under accession code of 409W.

Example 10

NCAPG2 Expression in Cancer Cells

For the evaluation of NCAPG2 expression level in cancer cells, normal human mammary epithelial cell (HMEC) and immortalized breast cancer cell lines (MCF10A) were cultivated, and then RT-PCR was performed with RNAs extracted from each cells. We also analyze the expression patterns of NCAPG2 and PLK1 and correlate the patterns with tumor patterns using Expression Atlas database.

NCAPG2 Functions in the Proper Spindle Attachment

Although NCAPG2 has been less studied compared with NCAPD3, this subunit is predicted to play important roles similar to the other condensin subunits. To analyse the role of NCAPG2 in mitosis, we employed *C. elegans*, which is a simple metazoan that has a NCAPG2 homologue, capg-2, and well-conserved condensin I and II complexes. We depleted capg-2 expression using a bacteria-feeding RNAi method. Consequently, chromosome segregation defects occurred in both germ cells and embryos (FIGS. 1A and 1B), and these defects were similar to previously reported findings (Csankovszki, G. et al. Three distinct condensin complexes control *C. elegans* chromosome dynamics. *Curr Biol* 19, 9-19 (2009)). Proper chromosome segregation requires accurate orientation of the bipolar spindle attachment to the kinetochore, which is an early event. Therefore, we examined CAPG-2 function when the microtubule-kinetochore dynamics were blocked by nocodazole, which interferes with microtubule polymerisation. Nocodazole did not directly affect mitosis, and most embryos from the nocodazole-treated worms developed normally. However, combining the nocodazole treatment with capg-2 RNAi induced more severe defects during mitosis in early embryos than capg-2 RNAi alone (FIG. 1B). Moreover, the survival ratio of the progeny from adult worms after the sequential treatment of capg-2 RNAi feeding plus nocodazole was significantly reduced compared with the treatment with capg-2 RNAi feeding alone (FIG. 1C). This synergistic result suggests that CAPG-2 may function in the microtubule-kinetochore interaction during mitosis. Next, we observed the first cleavage process of embryos as a time course to determine the initial defect caused by CAPG-2 depletion during mitotic progression. Although chromosome condensation still occurred during mitosis, chromosome alignment at the metaphase plate was defective in CAPG-2-depleted embryos (FIG. 1D). Surprisingly, spindle attachment to the chromosome tended to be disoriented with capg-2 RNAi feeding (FIG. 1E). These results suggest that capg-2 is involved in the proper orientation of the spindle attachment to the chromosomes in *C. elegans*.

Figure 2A:
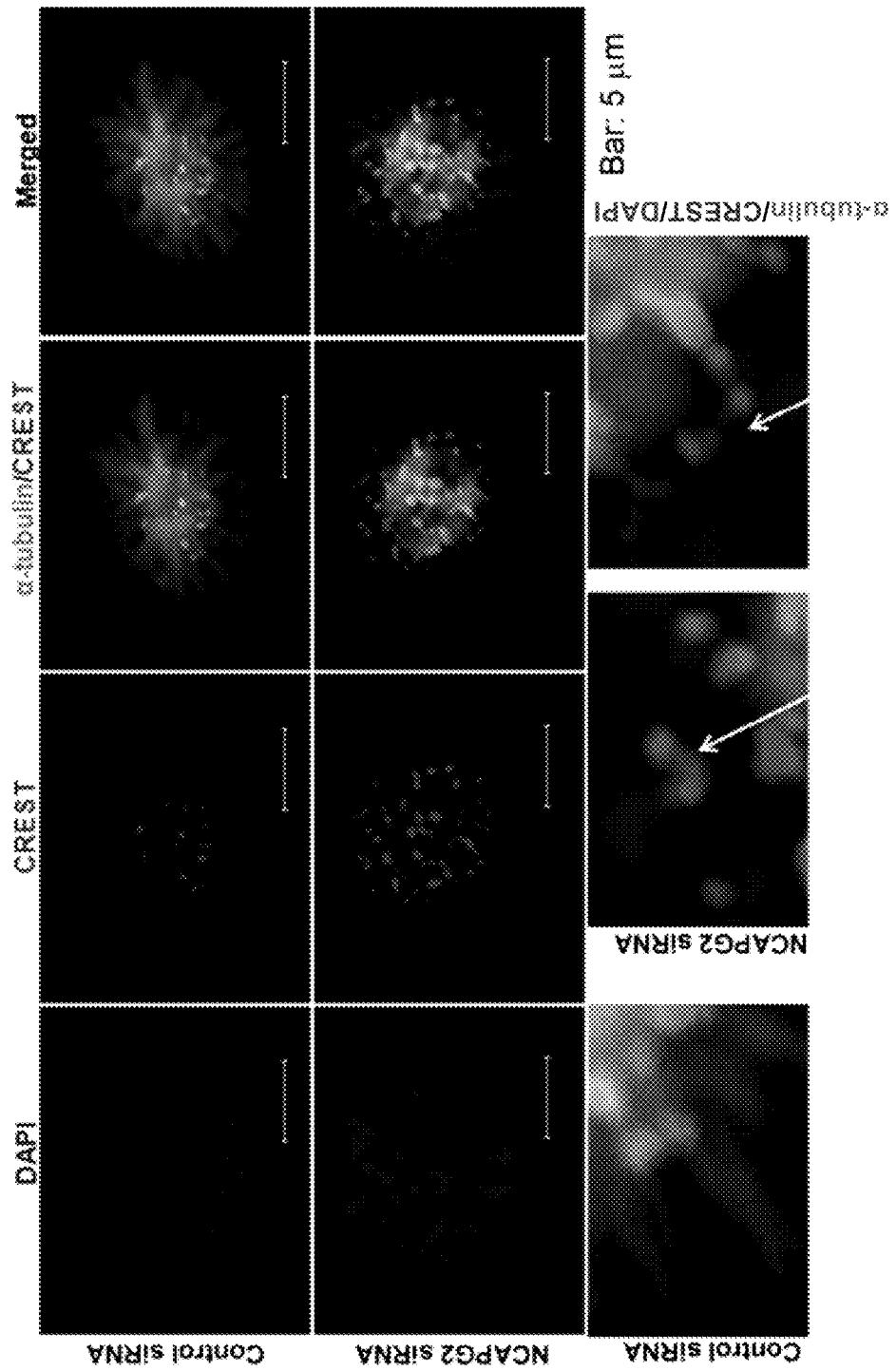
Figure 2B:
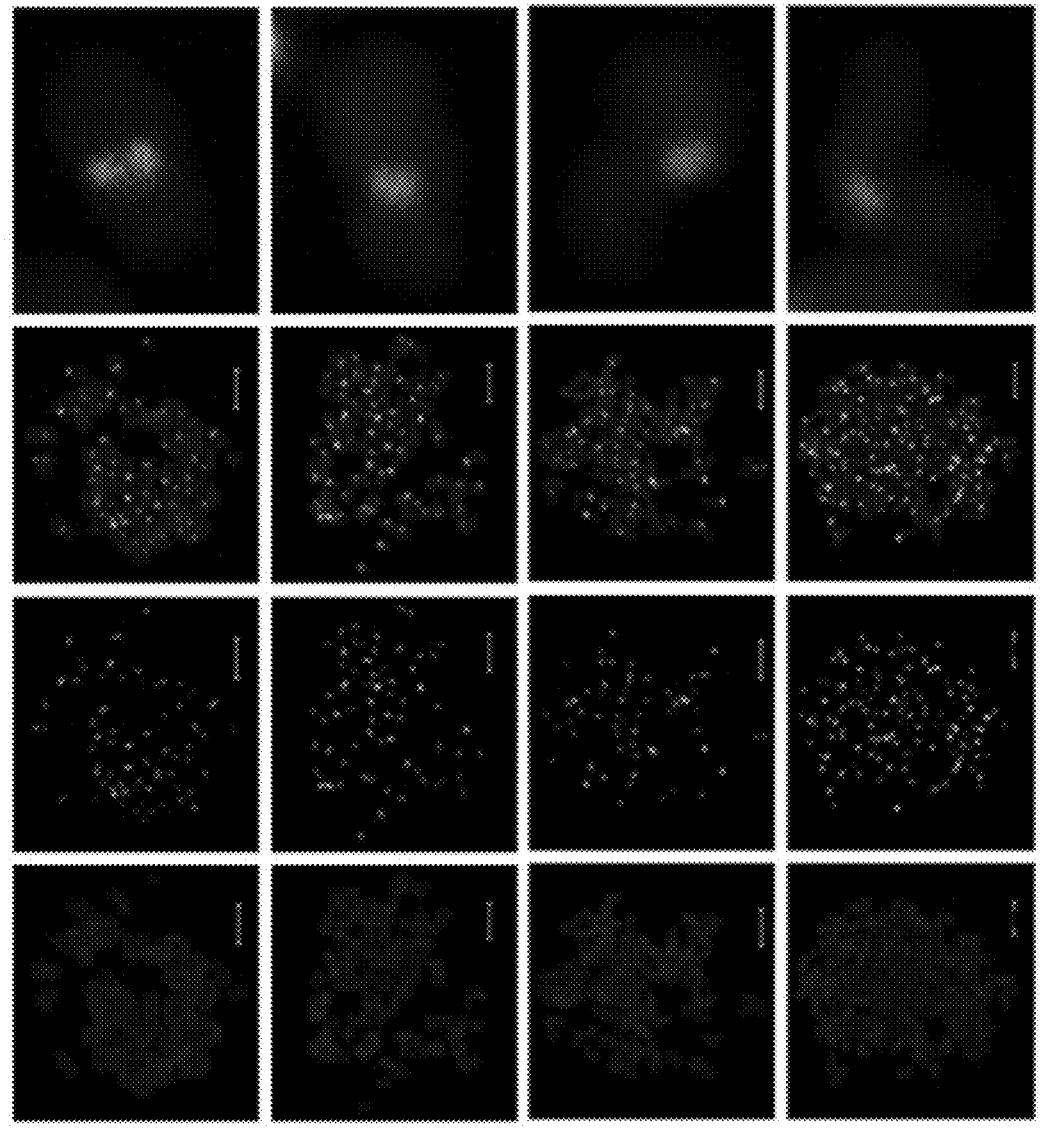

To further examine the role of NCAPG2 in the microtubule-kinetochore interaction, we observed this interaction following treatment with monastrol, which is an Eg5 spindle motor protein inhibitor that effectively blocks the bipolarity of mitotic spindles in mammalian cells[30]. Similar to our previous observation in *C. elegans*, monastrol treatment resulted in deteriorated microtubule-chromosome interactions in NCAPG2-depleted MDA-MB-231 cells (FIG. 2A). These defective microtubule-kinetochore interactions resulted in complications during chromosome segregation. Centromere FISH showed that NCAPG2-depleted cells treated with nocodazole possessed multiple centromeres compared with the control cells (FIG. 2B). To conform this result, we counted the metaphase spread chromosome with NCAPG2 knockdowned with either vehicle or nocodazole treatment. Cell population with a chromosome number greater more than 150 was increased by depletion of NCAPG2 expression, and the counts were further increased by nocodazole treatment which is similar to increased mitotic defects by microtubule inhibitors in *C. elegans* (FIG. 2C). These results show that the NCAPG2 may contribute microtubule kinetochore interaction and play critical roles for chromosome segregation in both nematode and human.

NCAPG2 Functions in BubR1 Kinetochore Localization

Figure 3A:
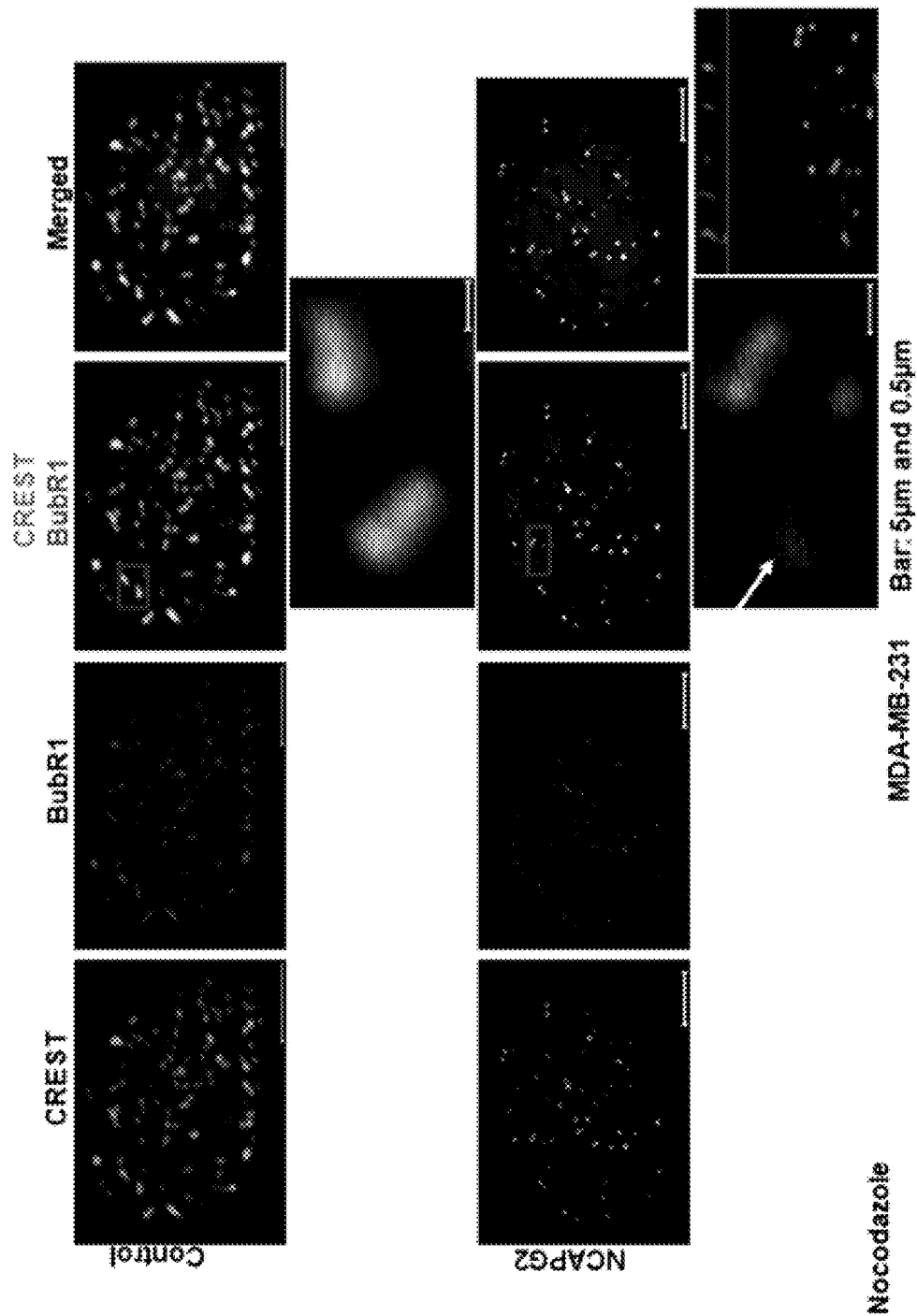
FIGS. 3A to 3C illustrate NCAPG2 contributes Plk1-BubR1 interaction in kinetochores.
Figure 3B:
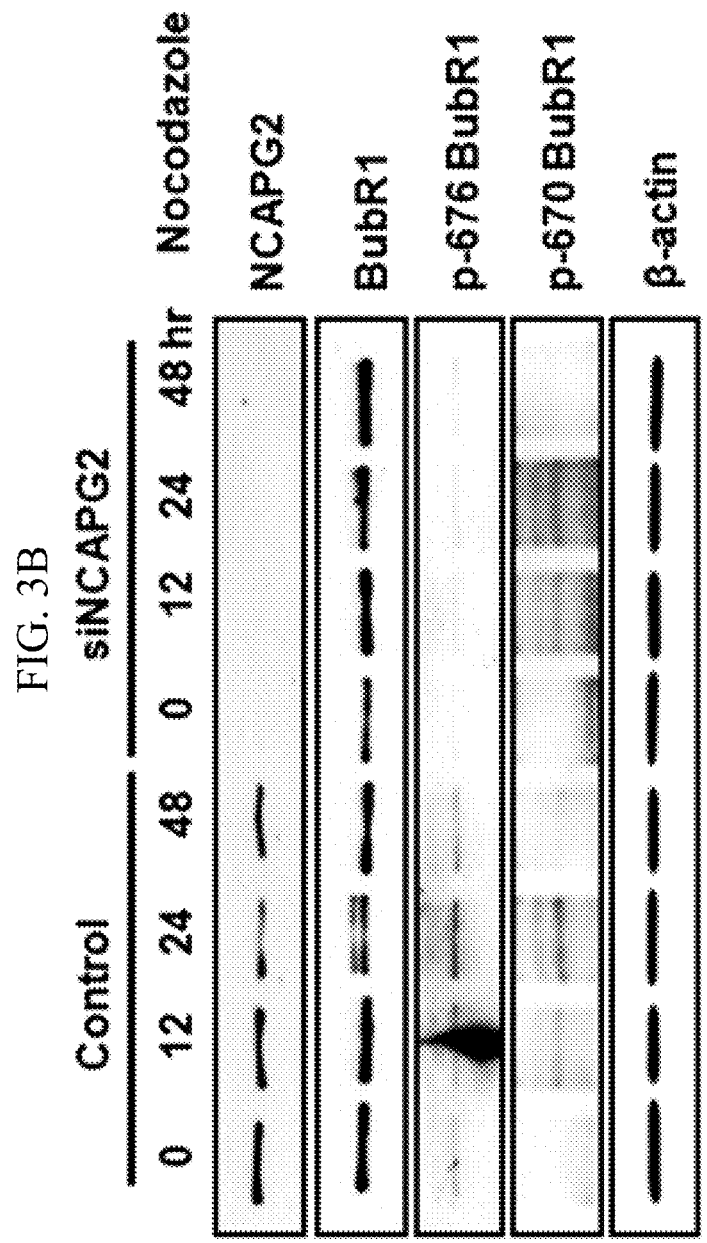
Figure 3C:
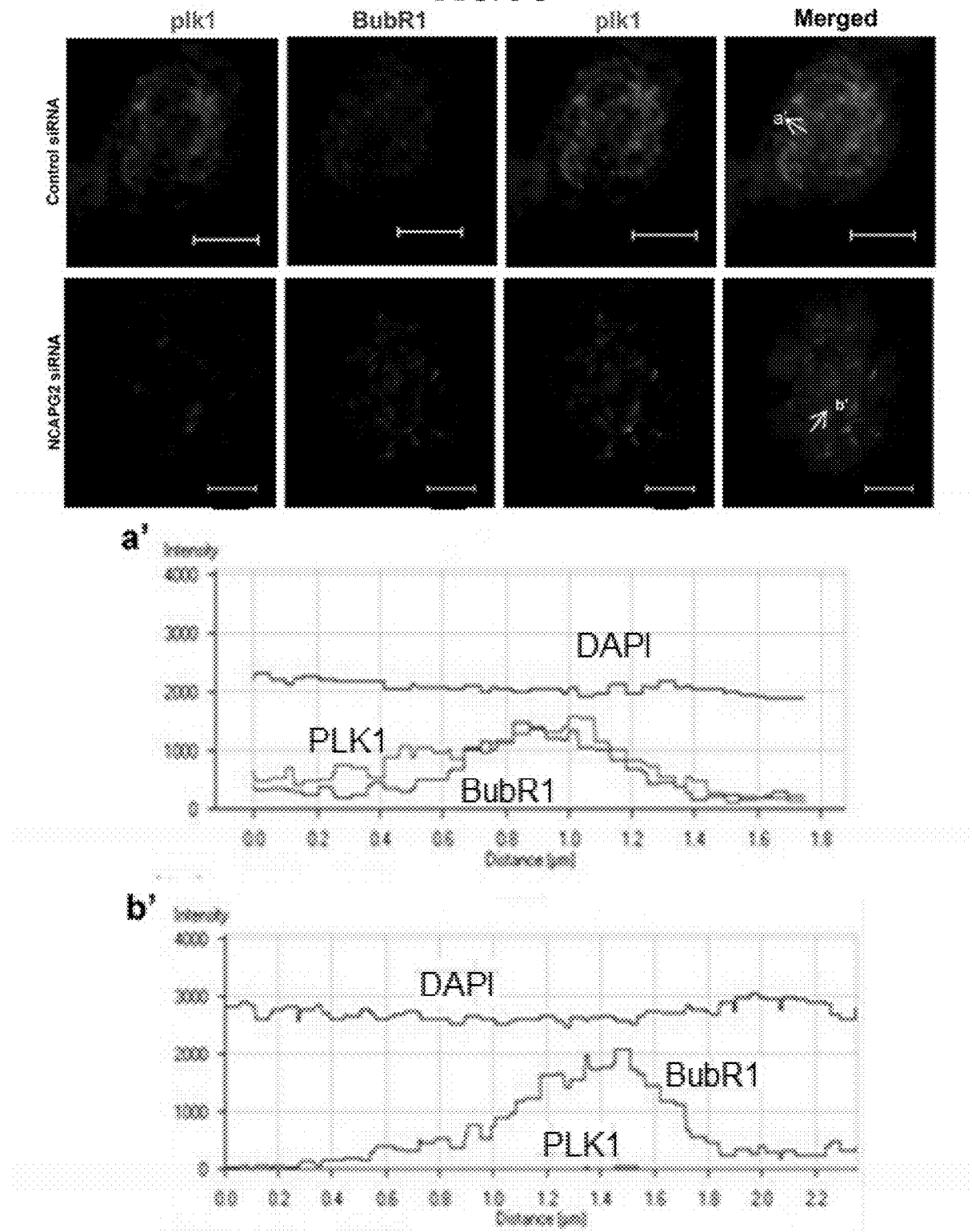

To examine the effect of NCAPG2 function on microtubule-chromosome interactions, we monitored the subcellular localization and phosphorylation of BubR1, which is one of the key kinetochore proteins mediating microtubule-kinetochore attachments. From prometaphase to anaphase, BubR1 localises at the kinetochore in a dumbbell-like manner. Interestingly, the depletion of NCAPG2 clearly interferes with BubR1 localization at the kinetochore (FIG. 3A). We note that BubR1 phosphorylation by PLK1 at the kinetochore is important for facilitating proper interactions between chromosomes and microtubules. Thus, we further examined the effect of NCAPG2 depletion on the functional interaction between BubR1 and PLK1 regarding kinetochore localization. Importantly, NCAPG2 depletion also disrupted PLK1 localization at the kinetochore (FIG. 3A). Furthermore, BubR1 phosphorylation at Ser676, which is a known substrate residue of PLK1, decreased in NCAPG2-depleted cells (FIG. 3B). These results indicate that NCAPG2 may be required for PLK1 recruitment to the kinetochore to allow the functional interaction with BubR1.

NCAPG2 is Required for PLK1 Localization at the Kinetochore

Figure 4:
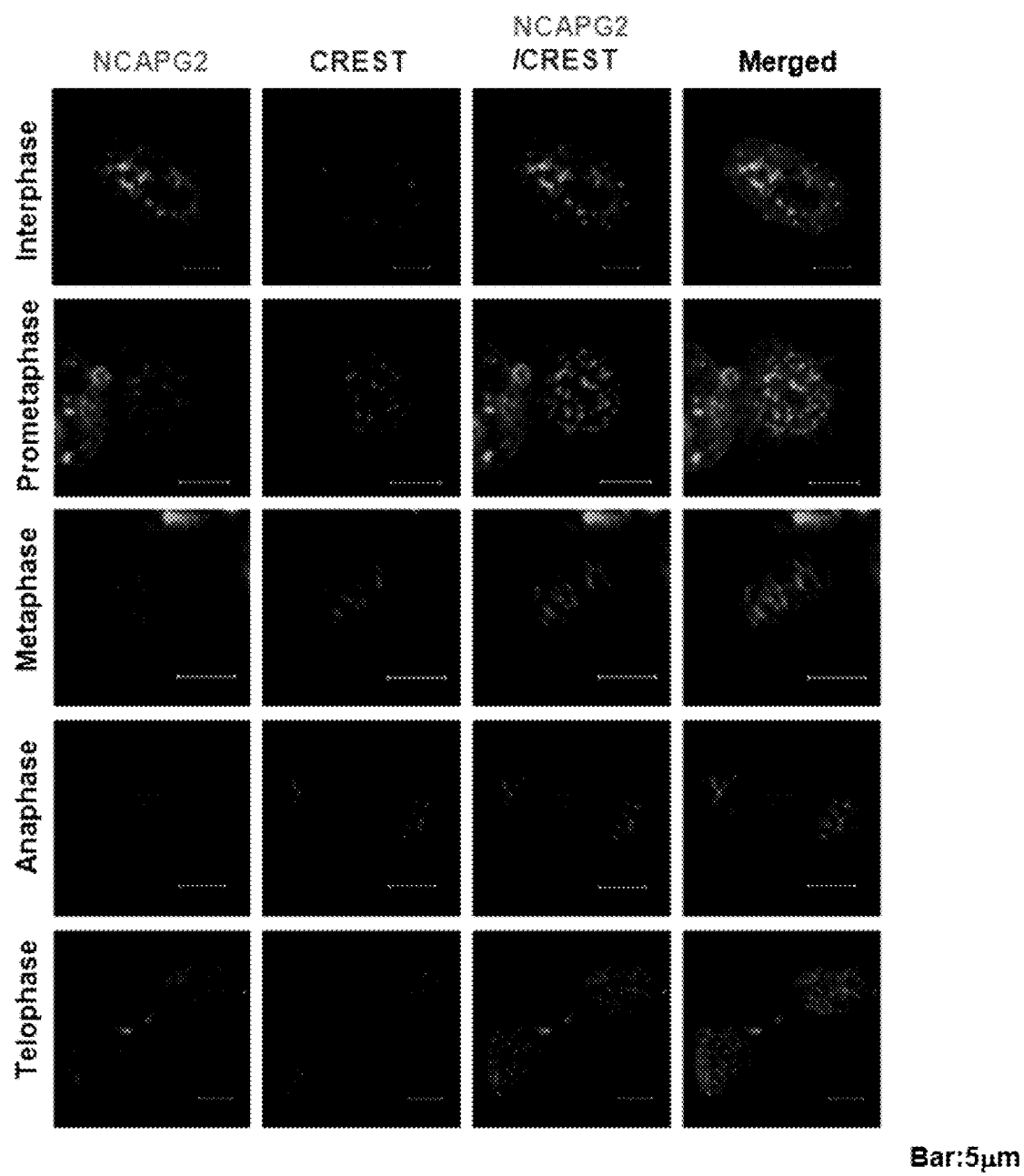
FIG. 4 illustrates NCAPG2 localization during cell cycle detected from immunostaining.

To verify that mis-localization of BubR1 results from disappearance of PLK1 at kinetochore, we investigated whether NCAPG2 affects localization of PLK1 at the kinetochore. Before the examination of PLK1 localization, NCAPG2 localization was identified during mitosis. NCAPG2 localized in nucleus and broadly spread during the interphase. When mitosis started, NCAPG2 was strongly spotted during the prometaphase at the center of chromosome that is co-stained with a kinetochore marker, CREST (FIGS. 4 and 6A). During the metaphase, kinetochore localization of NCAPG2 disappeared except the misaligned kinetochore. As mitosis progressed, NCAPG2 moved to spindle midzone, and outside of midbody (FIG. 4). This NCAPG2 localization closely correlated with microtubule after prometaphase.

Figure 6D:
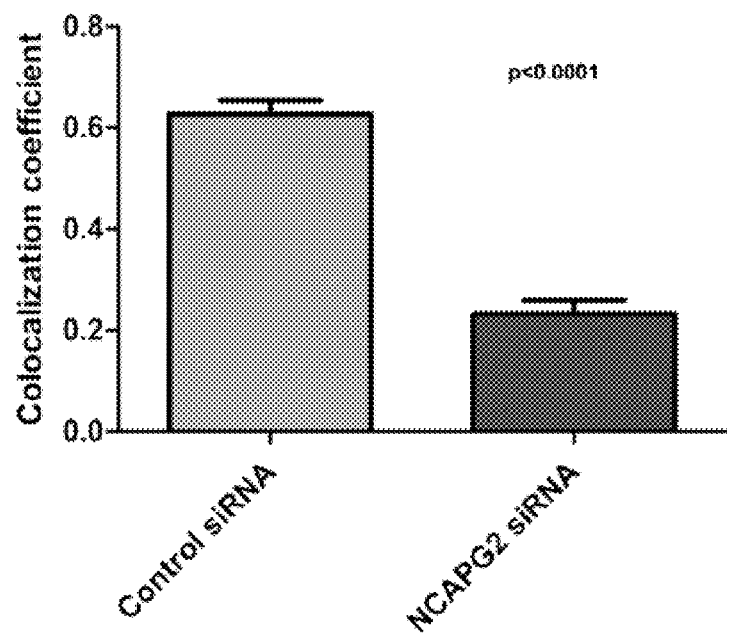
Figure 6E:
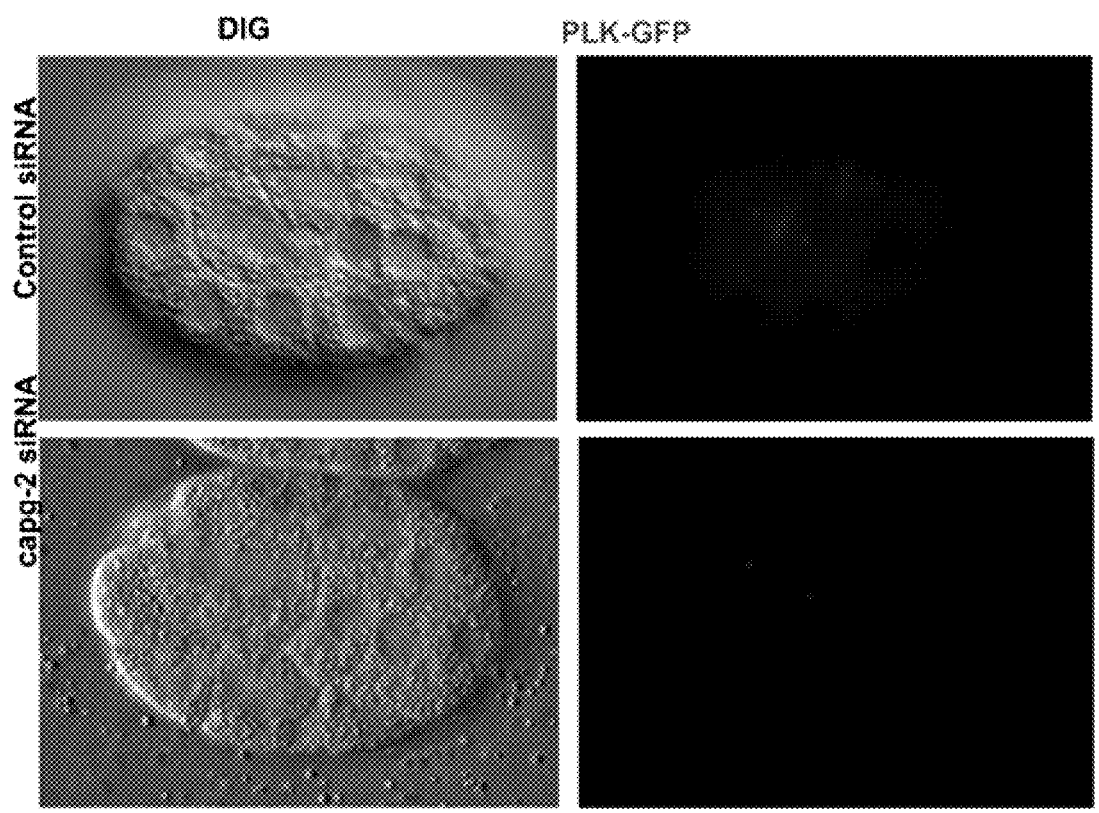
Figure 6F:
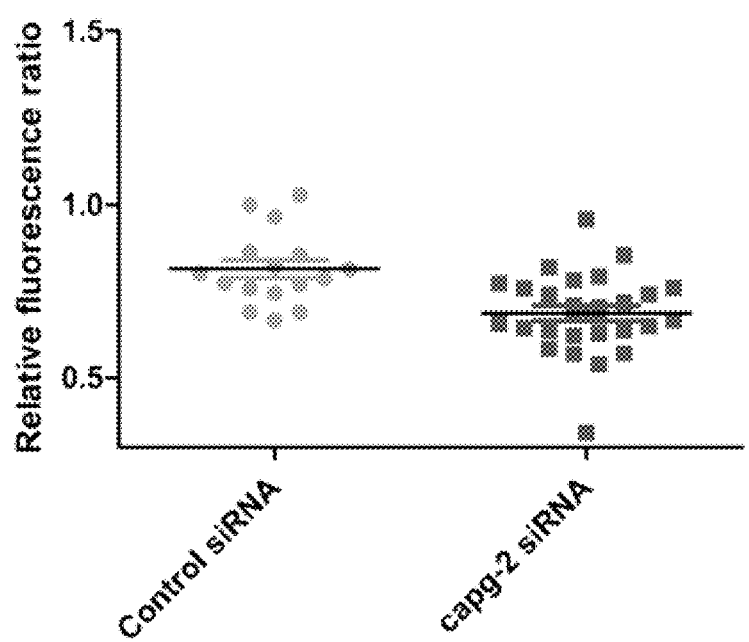

Interestingly, NCAPG2 co-localized with PLK1 at the kinetochores only in prometaphase or just remained in unaligned chromosome in metaphase (FIGS. 5 and 6B). After completion of chromosome alignment in the metaphase plate, NCAPG2 and PLK1 mutually exclusive staining pattern even though both proteins tightly interacted with microtubule (FIG. 5). To examine whether this interaction contributes to PLK1 localization into kinetochores, we measured the fluorescence intensity of anti PLK1 immunostained pseudo color image relative to intensity of anti CREST immunostained pseudo color images of either with control or NCAPG2 siRNA-treated cells. When NCAPG2 expression down regulated by siRNA, PLK1 localization coefficient with CREST was significantly lowered than the coefficient obtained from the control (FIGS. 6C and 6D). We confirmed this relationship between NGAPG2 and PLK1 localization at chromosome segreggation using in vivo C. elegans model (FIG. 6E). The PLK1 homolog in C. elegans, PLK-1 was expressed at both holocentric chromosome and centrosomes simultaneously during the metaphase (Nishi et al., 2008). GFP::PLK-1 is localized at whole holocentric chromosomes in the control, but GFP::PLK-1 was very weak at chromosomes in the capg-2 knockdowned embryo. To quantify the fluorescence of GFP::PLK-1 in the chromosomes and centrosomes in metaphase either capg-2 RNAi or control RNAi. The relative fluorescence ratio, GFP::PLK-1 intensity of chromosomes compared to that of centrosomes, was significantly reduced in capg-2 depleted embryos compared to control embryos (FIG. 6F). This result is consistent with the relative fluorescence coefficient experiment in human cells, even though their kinetochore structure of human cell is different from that of C. elegans. However, PLK1 localization into the midzone and midbody during cytokinesis was not affected by depletion of NCAPG2 expression. These results suggest that NCAPG2 may be a critical tractor for PLK1 localization in kinetochore and play important roles in microtubule kinetochore interaction.

NCAPG2 Binds to PLK1 Through PBD Domain

Figure 7A:
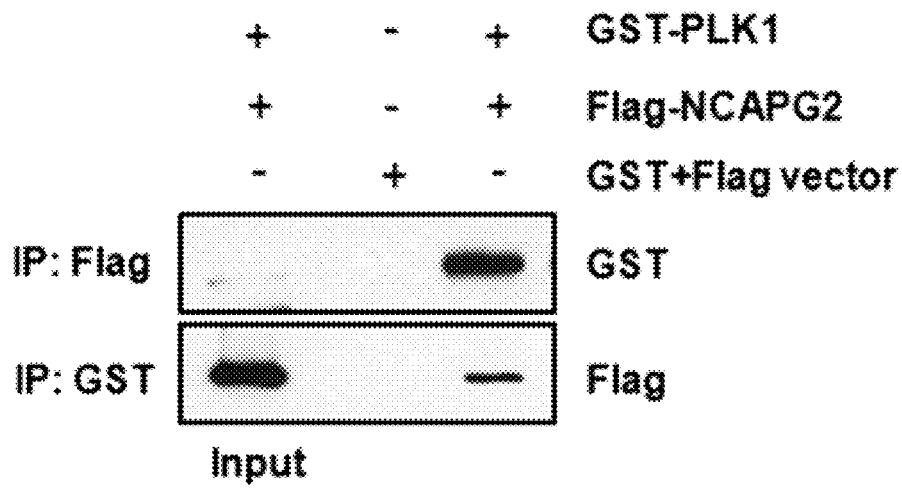
FIGS. 7A to 7D illustrate NCAPG2 binds to PLK1 directly.
Figure 7B:
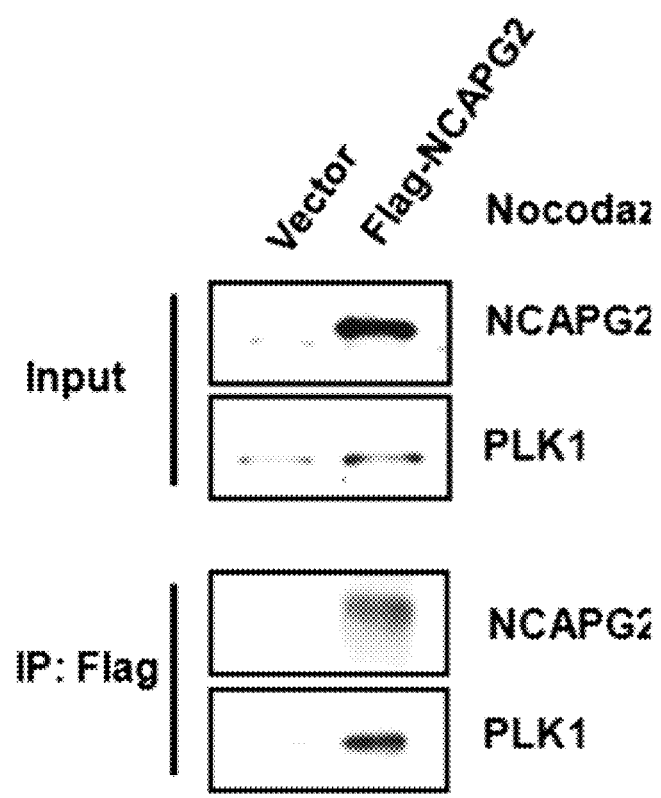
Figure 7C:
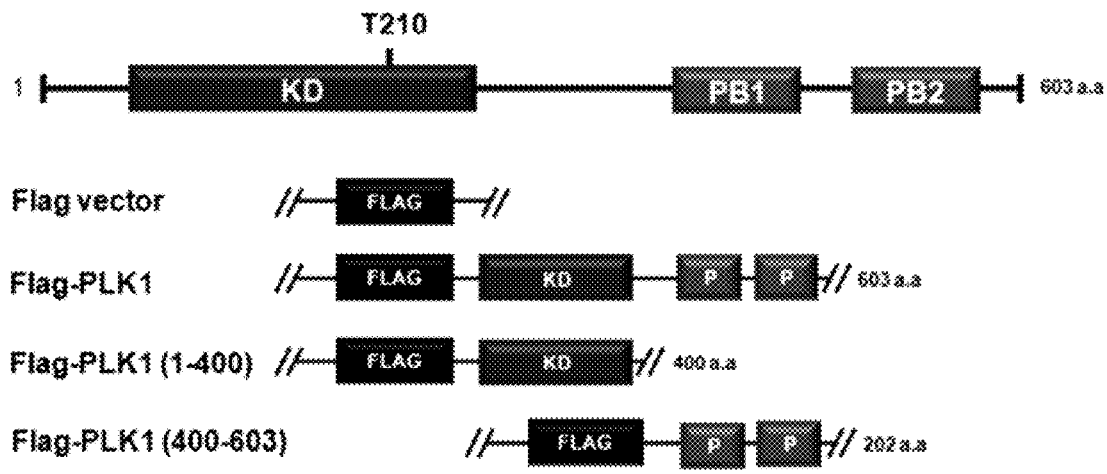
Figure 7D:
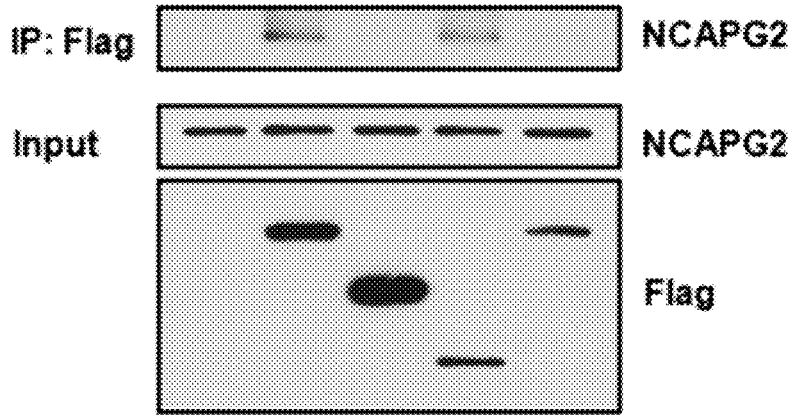

Since NCAPG2 recruits PLK1 into kinetochore, we examined the whether NCAPG2 physically interact with PLK1. When GST-PLK1 and Flag-NCAPG2 expressed and pull down with each bead, we could detect the interaction between the two proteins (FIG. 7A). Moreover, endogenous PLK1 was immune-precipitated with Flag-NCAPG2 under the nocodazole treatment condition (FIG. 7B). To explore the NCAPG2 binding region of the PLK1, we prepared various deletion mutants of Flag-PLK1 and performed pull-down experiment using the Flag bead (FIG. 7C). We could find that Polo box domain (PBD) was responsible for interaction with NCAPG2. In addition, PBD domain but substrate non recognizable FAA mutant was not co-precipitated with NCAPG2 (FIG. 7D). Furthermore, in vitro kinase assay using the purified PLK1 and NCAPG2 showed that NCAPG2 is directly phosphorylated by PLK1.

NCAPG2 1010T Position is Critical for PLK1 Binding

Because NCAPG2 is bound to PBD of PLK1, we attempted to identify which region of the NCAPG2 binds to PLK1. Pull down experiments showed that PLK1 binds strongly to full-length NCAPG2, suggesting that PBD domain of PLK1 interact with the C-terminal region (residues 714-1143) of NCAPG2 (FIG. 8A). Because it has been known that PBD of PLK1 preferentially binds to strictly conserved serine residue followed by phosphorylated serine or threonine residue (S-pS/T motif) for its proper functions in mitosis, we explored the S-pS/T motif in C terminal region of NCAPG2 and found that Thr1010 region of NCAPG2 is strictly conserved across the mammals to C. elegans (FIG. 8B). When Thr1010 was replaced with alanine, PLK1 interaction was significantly decreased (FIG. 8D). This decreased binding affinity by non-phosphorable mutant implied the possibility of phosphorylation dependent interaction.

To test whether this binding is direct and in a phosphorylation dependent manner, we performed fluorescence polarization in vitro binding assay using the synthetic peptides (FIG. 8C). In contrast to unphosphorylated 7-mer peptide ($^{1006}$GVLSTLI$^{1012}$, SEQ ID NO: 8), the phosphorylated peptide ($^{1006}$GVLS-pT-LI$^{1012}$) interacts strongly with PBD of PLK1 with Kd value of 69.91±15.95 nM. We also visualized the localization of NCAPG2 with the phosphorylated Thr1010 in chromosome and kinetochore (FIG. 8E). The NCAPG2 was seen on chromosome during early stage of mitosis. However, its expression decreased, and then it was seen only near centromere in telophase.

We also performed pull down assay with PLK1 and the NCAPG2 mutant (T1010A) which substituted threonine with alanine at the residue number 1010 of SEQ ID NO: 7. The binding of the T1010A mutant to PLK1 was inhibited.

Figure 9A:
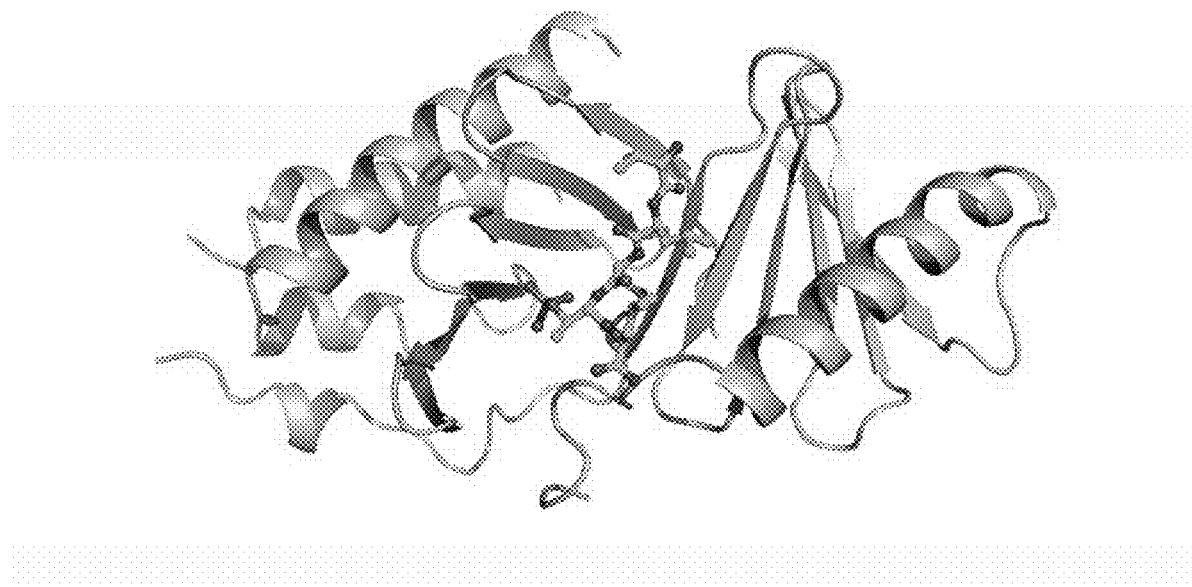
FIGS. 9A and 9B illustrate crystal structure of PBD in complex with the 1010pT peptide. The 1010pT peptide binds to the shallow cavity formed by interface of the two PBs.
Figure 9B:
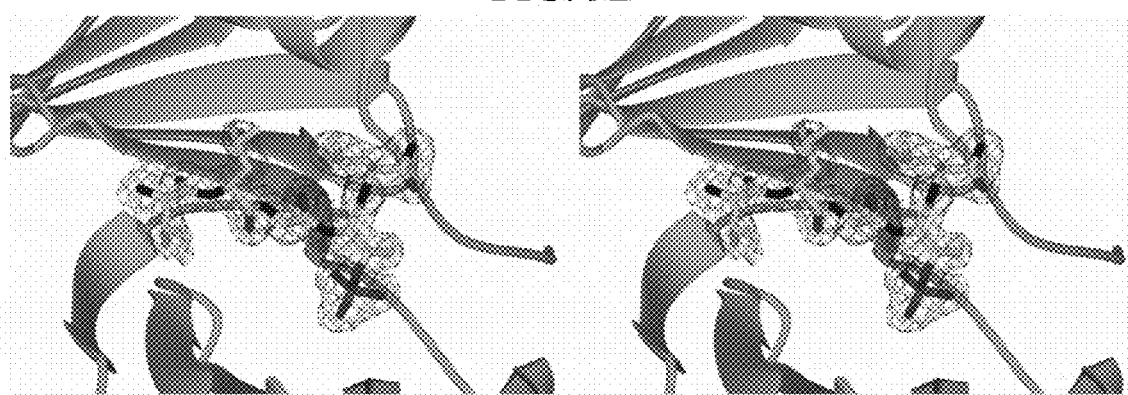
Figure 9C:
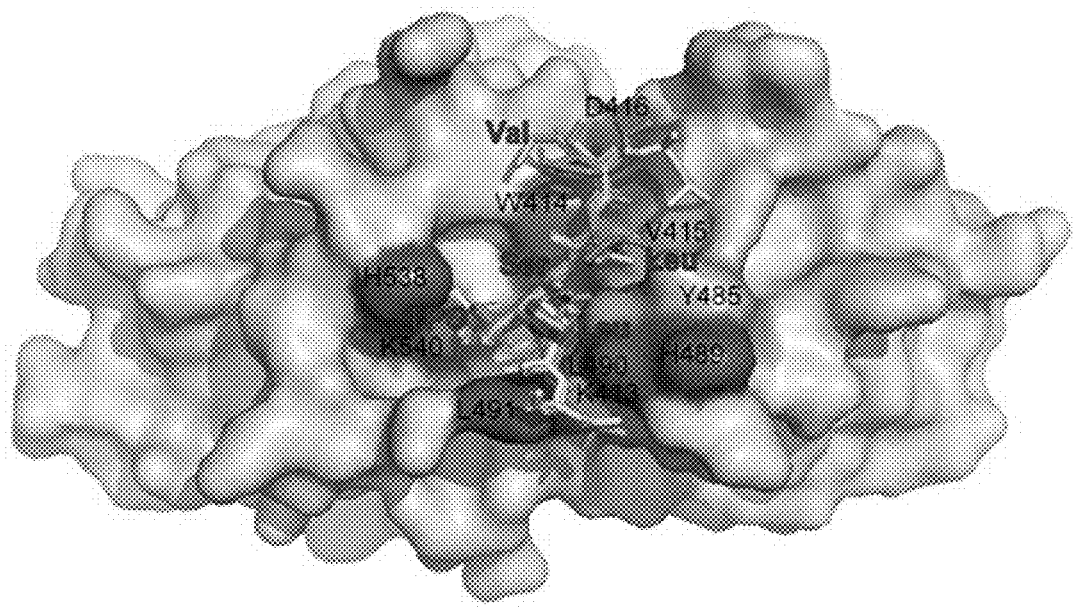
FIG. 9C shows the superimposed view of PBD-phosphopeptide complexes. The PBD-1010pT peptide (PDB entry: 4O9W) is labelled in red and drawn in green, the PBD-PBIP peptide (PDB entry: 3FVH) is drawn in orange, the PBD-synthetic optimal peptide (PDB entry: 1Q4K) is drawn in pink, and the PBD-Cdc25C peptide (PDB entry: 3OJS) is drawn in yellow. The residues of PBD that interact with the 1010pT peptide through hydrogen bonds or through hydrophobic contacts are labelled in black and represented in blue or in pink, respectively.
Figure 9D:
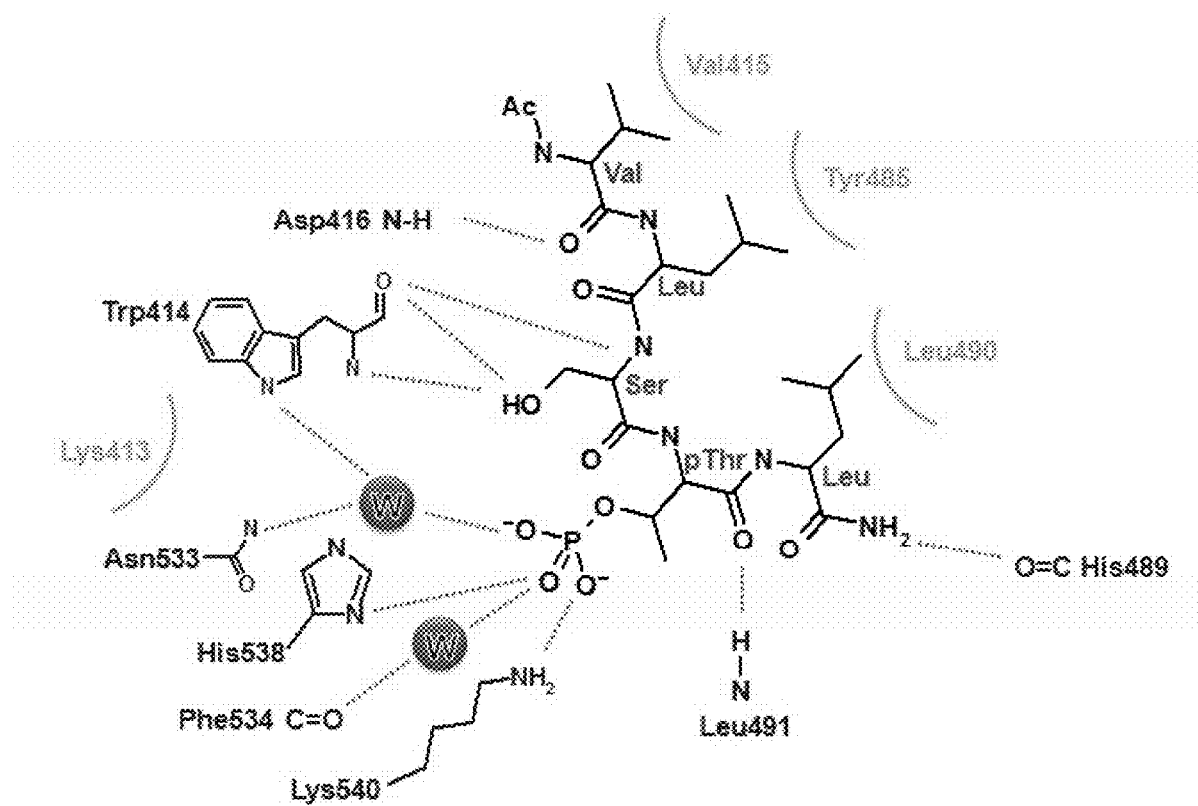
FIG. 9D shows the schematic diagram of the 1010pT peptide-binding mode. 'W' represents a water molecule.

Furthermore, we determined the crystal structure of PBD of PLK1 in complex with the 5-mer phosphopeptide VLS-pT-L at 1.8 Å resolution (FIG. 9A). The PBD structure shows the typical architecture as previously reported structures (Elia et al., 2003; Cheng et al., 2003; Garcia-Alvarez et al., 2006; Yun et al., 2009). Several antiparallel β-sheets from the two PBs generate the shallow cavity allowing the substrate binding (FIG. 9B). The binding mode of peptide to PBD of PLK1 is highly similar to other PBD:phosphopeptide complexes (FIG. 9C). The overall conformation of substrate peptides was conserved. Especially, Ser-pThe motif shows strictly conserved conformation. The phosphothreonine residue (pT1010) forms hydrogen bonds with His538 and Lys540, like to other PBD:phosphopeptide structures (Llia et al., 2003; Chen et al., 2003; Garcia-Alvarez et al., 2006) (FIG. 9D). And the Trp414, which plays important roles for centrosome localization and substrate binding without affecting the kinase activity (Lee et al., 1998 PNAS; Liu et al., 2004 JBC), make multiple hydrogen bonds with serine residue of the substrate peptide, in direct or water-mediated manners. (FIG. 9D). Moreover, a lot of water molecules found near the phospho-threonine residue make hydrogen bond network and strengthen the binding affinity, similar to PBD-Cdc25C primed peptide structures (Garcia-Alvarez et al., 2006; FIG. 9D; cartoon for binding mode). A water molecule mediate hydrogen bond network with Trp414 and oxygen atom of phosphate and another water molecule forms hydrogen bond with carbonyl oxygen of Phe534 and oxygen atom of phosphate in substrate peptide (FIG. 9D). Additionally, Asp416, His489 and Leu491 also participate in formation of hydrogen bonds and Lys413, Val415, Tyr485 and Leu490 forms hydrophobic contacts with 1010pT peptide. Interestingly, the CL loop, that connects the two PBs (residue 493-507; referred in Garcia-Alvarez et al., 2006) and usually is ordered upon phosphopeptide binding, was partially disordered in our structure. Moreover, nine residues between the residue 499 and 507 were missing in our structure.

As the NCAPG2 1010T position is critical for PLK1 binding, we performed reconstitution experiments after NCAPG2 siRNA transfection. For the reconstitution experiment, lenti-viral siRNA resistant NCAPG2 wild type or T1010A mutant expression vector (NCAPG2$^{R-Wt}$ or NCAPG2$^{R-T1010A}$) were constructed. When NCAPG2 expression depleted, PLK1 localization into kinetochore disappeared. Whereas, wild type NCAPG2 reconstitution retrieved PLK1 localization into kinetochore, but T1010A mutant was not able to recover PLK1 into kinetochore (FIG. 10A). This unsuccessful reconstitution of PLK1 localization into kinetochore by T1010A NCAPG2 mutant was conformed from relative fluorescence intensities measurement of PLK1 staining in kinetochore in comparison with anti-CREST staining (FIG. 10B). In addition, BubR1 phosphorylated shift band in western blotting after nocodazole treatment weaken by T1010A mutant not in wild type NCAPG2 reconstitution (FIG. 10C). These results suggested that NCAPG2 T1010 and its bearing region would be the critical for PLK1 interaction into kinetochore.

Figure 8F:
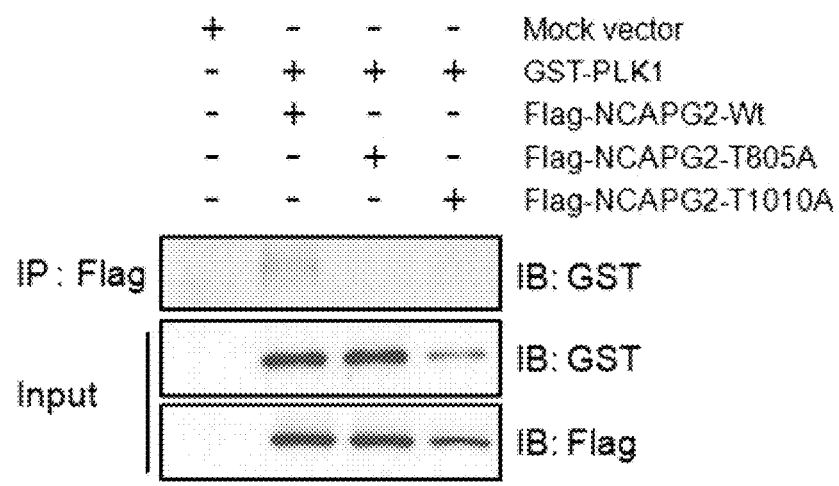

We also performed pull down assay for Flag-tagged NCAPG2 and the NCAPG2 mutant (T805A) which substituted threonine with alanine at the residue number 805 of SEQ ID NO: 7 with PLK1. The binding of the T805A mutant to PLK1 was inhibited, as was the case in the T1010A (FIG. 8F).

Expression of NCAPG2 in Tumor Cells

Figure 11A:
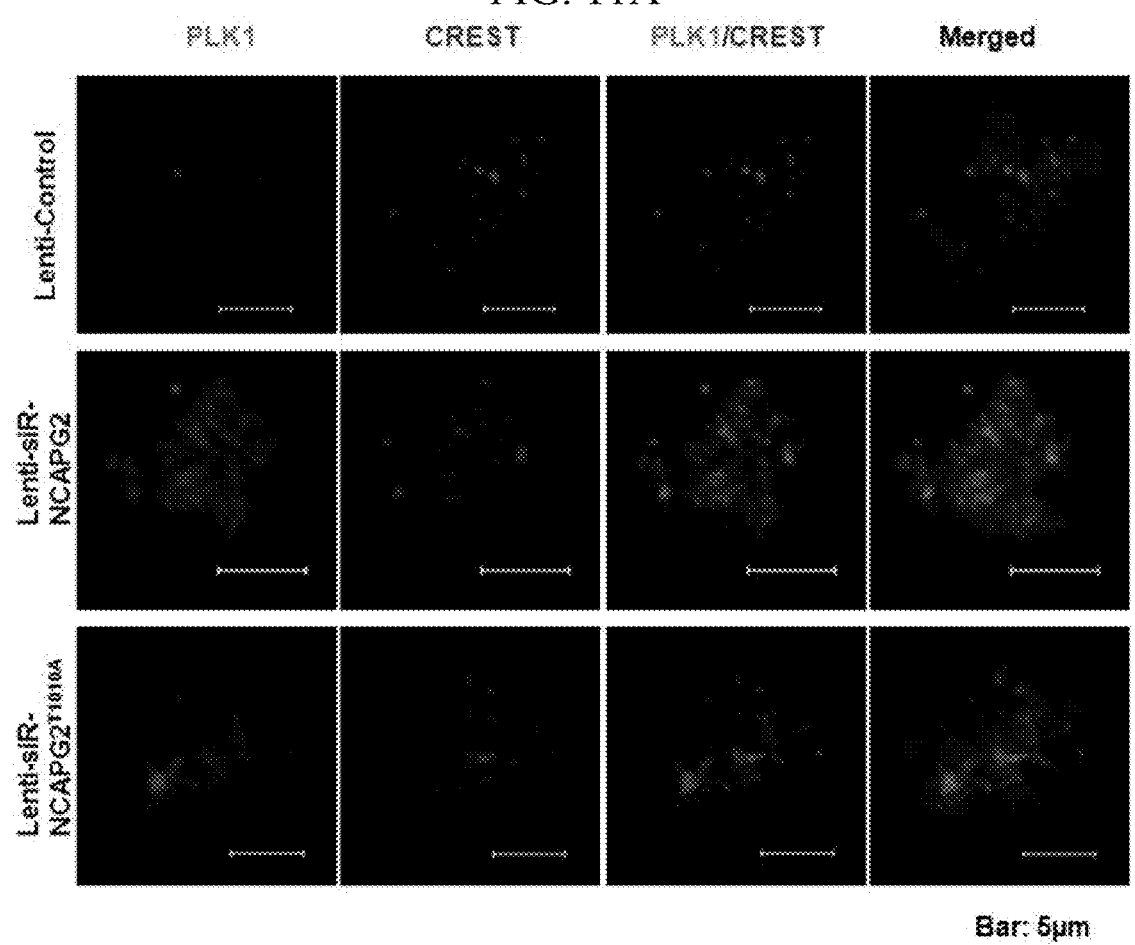
Figure 11B:
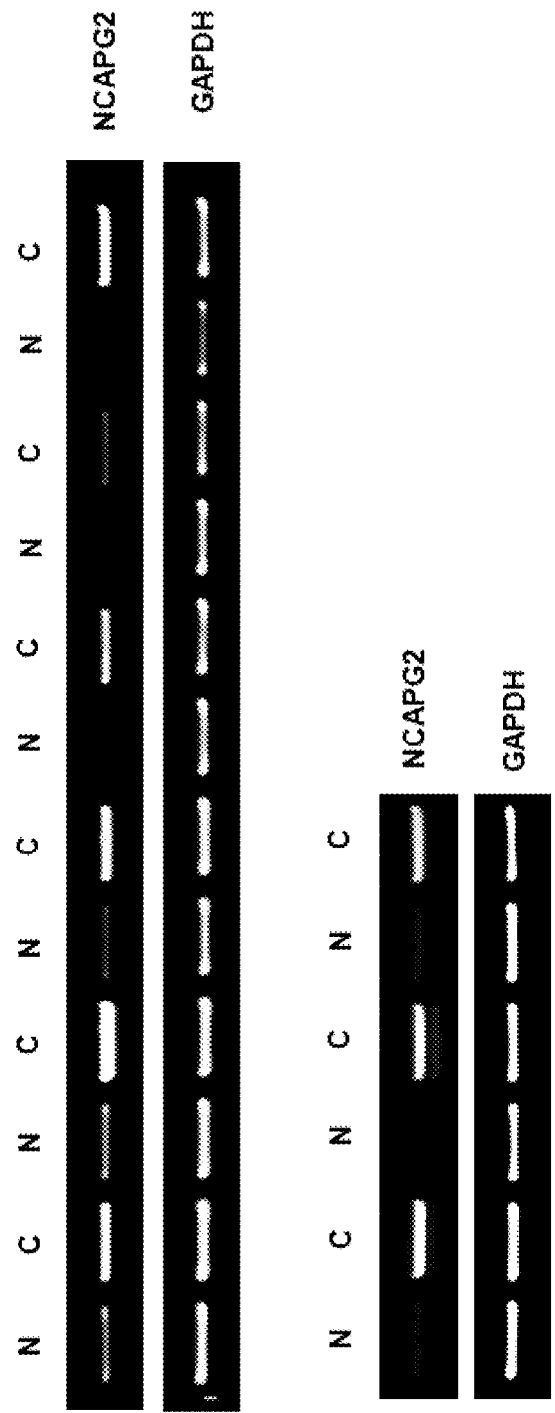

We performed RT-PCR with RNAs extracted from tumor cell lines or tissues to examine the expression level of NCAPG2. The expression of NCAPG2 in breast cancer cell line or tissue was significantly increased compared to the expression in normal cell or immortalized cell (FIGS. 11A, 11B, and 11D). We also confirmed that the expression of NCAPG2 in human colon cancer tissue, bladder cancer tissue or cell lines (FIG. 11E). The results indicate that the expression of NCAPG2 increased in carcinogenesis.

Thus, we schematized the expression patterns of various carcinomas based on the expression patterns of NCAPG2 and PLK1 using Expression Atlas database (FIG. 11C). According to the Expression Atlas database, the expressions of NCAPG2 and PLK1 tend to increase together in various carcinomas.

Anti-Tumor Activity of NCAPG2

As seen in FIG. 12, the NCAPG2 peptide comprising the amino acid residue number 1010 of SEQ ID NO: 7 (NG2 The1010: VLSTL) (SEQ ID NO: 11) and its phosphorylated peptide (NG2 pThe1010: VLSpTL) lowered survival rate of human liver cancer cell (HuR-7) and induced abnormal mitosis. We treated the liver cancer cell with FITC-tagged NG2 The1010 and NG2 pThe1010, and confirmed that the peptide entered the cell by observing the fluorescence of FITC. The number of cells decreased (FIG. 12), indicating that the NCAPG2 peptide suppresses the proliferation of cancer cell by inhibiting the function of PLK1.

The result suggests that NCAPG2 or the peptides according to the present invention can be used as an anti-tumor agent since they inhibit the normal mitosis of cancer cells by blocking the normal PLK1-Substrate binding by interacting with PLK1 when they are artificially delivered into the cancer cells, although the normal NCAPG2-PLK1 binding is necessary for mitosis.

1010pT Peptide Specifically Binds to PLK1

The human PLK1-PBD (371-594), PLK2-PBD (451-685) and PLK3-PBD (412-646) genes were cloned into pGEX6p-1 vector using EcoRI/XhoI restriction sites. Proteins were over expressed in E. coli strain Rosetta2 (DE3) pLysS. The cells were grown in Terrific Broth medium to an OD600 of 0.6 at 37° C. and recombinant proteins were induced with 0.1 mM isopropyl b-D-thiogalactopyranoside (IPTG) at 25° C. for PLK2 and 20° C. for PLK1 and PLK3, respectively. The cells were further grown at 25° C. (PLK2) or 20° C. (PLK1 and PLK3) for 20 h after IPTG induction. Each cell pellet was lysed with each PLK Binding buffer as described below. PLK1 Binding buffer (10 mM, 0.2 M NaCl, 3.4 mM EDTA, 0.01% thioglycerol), PLK2 Binding buffer (20 mM Tris-HCl pH 8.0, 500 mM NaCl, 1 mM β-mercaptothanol for PLK2) or PLK3 Binding buffer (20 mM Tris-HCl pH 7.5, 500 mM NaCl, 7 mM β-mercaptothanol, 10% glycerol). GST fused PLK-PBD proteins were purified using glutathione-Sepharose resin. The resins were washed using each PLK Binding buffer and protein was eluted with each Binding buffer complemented with 20 mM glutathione. The GST tag was cleaved by 3C protease. The mixture of GST and PLK-PBD proteins were further purified by HiLoad 16/600 Superdex 200 or 75 prep-grade columns and then passed through second glutathione-Sepharose column. The purified PLK-PBD proteins were concentrated and used for the fluorescence polarization binding assay.

For the fluorescence polarization binding assay, each fluorescein isothiocyanate (FITC)-labeled 1010pT (GVLSpTLI), 1010T (GVLSTLI), 1010E (GVLSELI), or 1010D (GVLSDLI) peptide was mixed with purified PLK1, PLK2 or PLK3 and incubated in a buffer containing 10 mM HEPES (pH 7.5), 50 mM NaCl, 1 mM EDTA, 1 mM DTT and 0.0025% (v/v) Tween 20. The final protein concentrations ranged from 0 to 4 uM, and the final peptide concentration was 10 nM. Fluorescence polarization was analyzed 30 min after mixing the peptide and proteins in a 96-well plate using an INFINTE 200 PRO (Tecan). Binding curves were fitted using the GraphPad Prism software.

Figure 13:
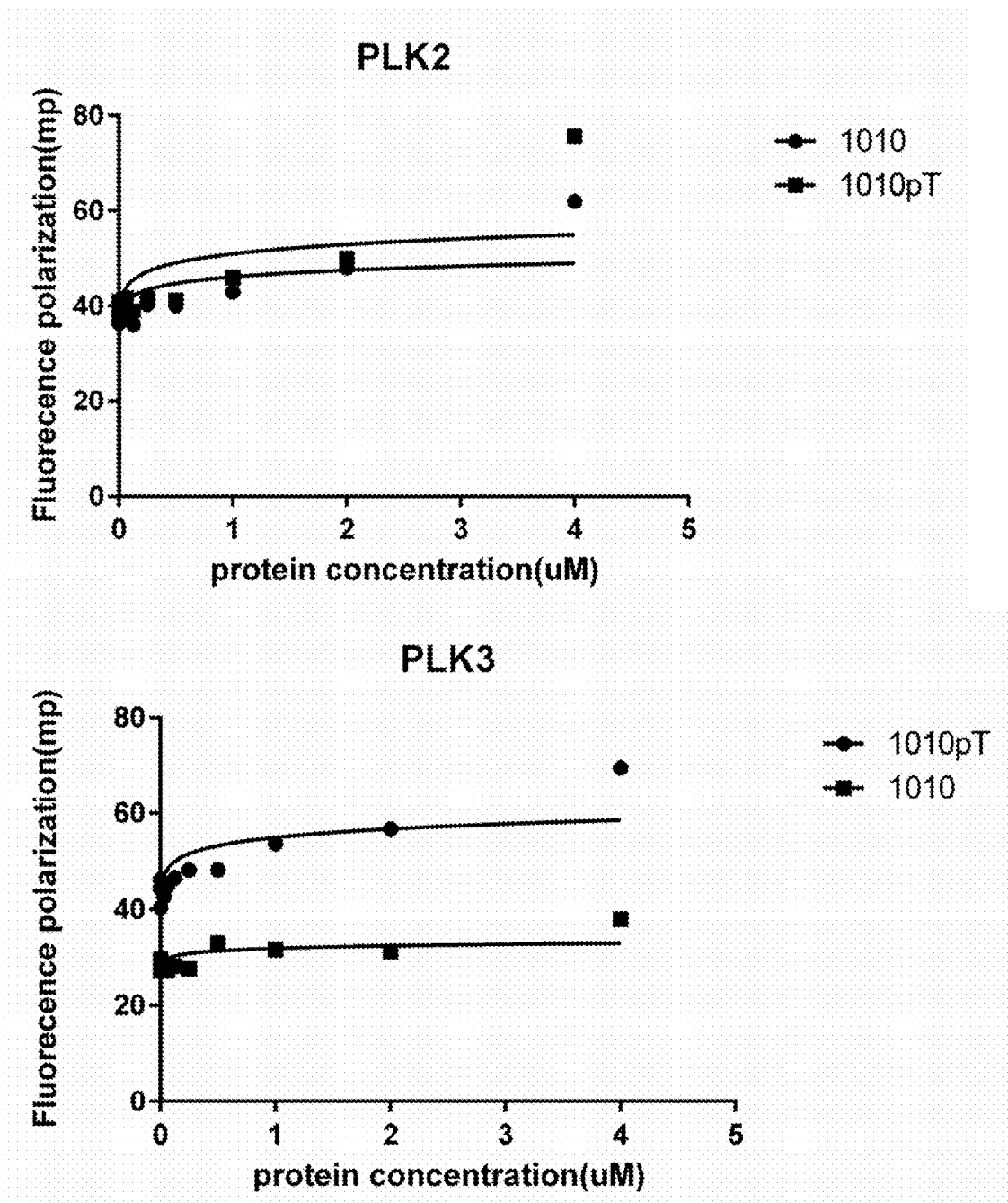

The 1010pT peptide exhibited high target selectivity across the PLK1-, PLK2-, and PLK3-PBD proteins. While PLK1 functions as oncogene and highly overexpressed in various cancer cells, PLK2 and PLK3 play roles as tumor suppressors although they share high amino acids sequence similarity. So, it is important that PLK1 inhibitors have target selectivity over PLK2 and PLK3 for good efficacy, low toxicities and side effects. As seen in FIG. 13, 1010pT peptide specifically binds to PLK1 and did not bind PLK2 and PLK3, suggesting the good target specificity.

Glutamate (E) or aspartate (D) frequently used for phosphor-Thr mimetic residues in biochemical studies. So, we tested if the substitution of phosphor-Thr to aspartate or glutamate will exhibit similar PLK1-PBD binding activity. As seen in FIG. 14, it might be helpful for discovery of peptide based PLK1-PBD inhibitor. But, 1010E and 1010D peptide did not bind PLK1-PBD and was not suitable for phosphor-Thr substitution.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present invention. It is noted that, as used in this specification and the appended claims, the singular forms "a," "an," and "the," include plural references unless expressly and unequivocally limited to one reference. As used herein, the term "include" and its grammatical variants are intended to be non-limiting, such that recitation of items in a list is not to the exclusion of other like items that can be substituted or added to the listed items.

This written description uses examples to disclose the invention, including the best mode, and also to enable any person skilled in the art to make and use the invention. The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. To an extent not inconsistent herewith, all citations referred herein are hereby incorporated by reference.

What is claimed is:

1. A method of treating a cancer in a subject in need thereof comprising administering a pharmaceutical composition comprising an effective amount of a peptide comprised of a fragment of the NCAPG2 protein as an active ingredient to the subject, wherein the peptide consists of the amino acid sequence of SEQ ID NOs: 8 or 11.

2. The method of claim 1, wherein the peptide consisting of the amino acid sequence of SEQ ID NOs: 8 or 11 has phosphorylated threonine.

3. The method of claim 1, wherein the peptide inhibits the normal mitosis of cancer cells by blocking the normal PLK1-Substrate binding by interacting with PLK1.

* * * * *

SEQUENCE LISTING

<160> NUMBER OF SEQ ID NOS: 11

<210> SEQ ID NO 1
<211> LENGTH: 21
<212> TYPE: DNA
<213> ORGANISM: Artificial Sequence
<220> FEATURE:
<223> OTHER INFORMATION: siRNA for NCAPG2

<400> SEQUENCE: 1
gcuucauagg gucauuuaut t                                                  21

<210> SEQ ID NO 2
<211> LENGTH: 21
<212> TYPE: DNA
<213> ORGANISM: Artificial Sequence
<220> FEATURE:
<223> OTHER INFORMATION: siRNA for NCAPG2

<400> SEQUENCE: 2
gaagaaugau gcugaaacat t                                                  21

<210> SEQ ID NO 3
<211> LENGTH: 60
<212> TYPE: DNA
<213> ORGANISM: Artificial Sequence
<220> FEATURE:
<223> OTHER INFORMATION: siR-NCAPG2 forward primer for Site-Directed
      Mutagenesis

<400> SEQUENCE: 3
gaagaagact acctgaagct tcacagagtg atttatcagc aaattatcca gacctacctg        60

<210> SEQ ID NO 4
<211> LENGTH: 60
<212> TYPE: DNA
<213> ORGANISM: Artificial Sequence
<220> FEATURE:
<223> OTHER INFORMATION: siR-NCAPG2 reverse primer for Site-Directed
      Mutagenesis

<400> SEQUENCE: 4
caggtaggtc tggataattt gctgataaat cactctgtga agcttcaggt agtcttcttc        60

<210> SEQ ID NO 5
<211> LENGTH: 28
<212> TYPE: DNA
<213> ORGANISM: Artificial Sequence
<220> FEATURE:
<223> OTHER INFORMATION: NCAPG2T1010A forward primer

<400> SEQUENCE: 5
ggggtgtact ttctgctctg atcgctgg                                           28

<210> SEQ ID NO 6
<211> LENGTH: 28
<212> TYPE: DNA
<213> ORGANISM: Artificial Sequence
<220> FEATURE:
<223> OTHER INFORMATION: NCAPG2T1010A reverse primer

<400> SEQUENCE: 6

```
ccagcgatca gagcagaaga tacacccc                                    28
```

<210> SEQ ID NO 7
<211> LENGTH: 1143
<212> TYPE: PRT
<213> ORGANISM: Homo sapiens

<400> SEQUENCE: 7

| Met | Glu | Lys | Arg | Glu | Thr | Phe | Val | Gln | Ala | Val | Ser | Lys | Glu | Leu | Val |
|---|---|---|---|---|---|---|---|---|---|---|---|---|---|---|---|
| 1 | | | | 5 | | | | | 10 | | | | | 15 | |

Gly Glu Phe Leu Gln Phe Val Gln Leu Asp Lys Glu Ala Ser Asp Pro
                20                  25                  30

Phe Ser Leu Asn Glu Leu Leu Asp Glu Leu Ser Arg Lys Gln Lys Glu
            35                  40                  45

Glu Leu Trp Gln Arg Leu Lys Asn Leu Leu Thr Asp Val Leu Leu Glu
    50                  55                  60

Ser Pro Val Asp Gly Trp Gln Val Val Glu Ala Gln Gly Glu Asp Asn
65                  70                  75                  80

Met Glu Thr Glu His Gly Ser Lys Met Arg Lys Ser Ile Glu Ile Ile
                85                  90                  95

Tyr Ala Ile Thr Ser Val Ile Leu Ala Ser Val Ser Val Ile Asn Glu
                100                 105                 110

Ser Glu Asn Tyr Glu Ala Leu Leu Glu Cys Val Ile Ile Leu Asn Gly
            115                 120                 125

Ile Leu Tyr Ala Leu Pro Glu Ser Glu Arg Lys Leu Gln Ser Ser Ile
    130                 135                 140

Gln Asp Leu Cys Val Thr Trp Trp Glu Lys Gly Leu Pro Ala Lys Glu
145                 150                 155                 160

Asp Thr Gly Lys Thr Ala Phe Val Met Leu Leu Arg Arg Ser Leu Glu
                165                 170                 175

Thr Lys Thr Gly Ala Asp Val Cys Arg Leu Trp Arg Ile His Gln Ala
            180                 185                 190

Leu Tyr Cys Phe Asp Tyr Asp Leu Glu Glu Ser Gly Glu Ile Lys Asp
    195                 200                 205

Met Leu Leu Glu Cys Phe Ile Asn Ile Asn Tyr Ile Lys Lys Glu Glu
210                 215                 220

Gly Arg Arg Phe Leu Ser Cys Leu Phe Asn Trp Asn Ile Asn Phe Ile
225                 230                 235                 240

Lys Met Ile His Gly Thr Ile Lys Asn Gln Leu Gln Gly Leu Gln Lys
                245                 250                 255

Ser Leu Met Val Tyr Ile Ala Glu Ile Tyr Phe Arg Ala Trp Lys Lys
            260                 265                 270

Ala Ser Gly Lys Ile Leu Glu Ala Ile Glu Asn Asp Cys Ile Gln Asp
    275                 280                 285

Phe Met Phe His Gly Ile His Leu Pro Arg Arg Ser Pro Val His Ser
290                 295                 300

Lys Val Arg Glu Val Leu Ser Tyr Phe His His Gln Lys Lys Val Arg
305                 310                 315                 320

Gln Gly Val Glu Glu Met Leu Tyr Arg Leu Tyr Lys Pro Ile Leu Trp
                325                 330                 335

Arg Gly Leu Lys Ala Arg Asn Ser Glu Val Arg Ser Asn Ala Ala Leu
            340                 345                 350

Leu Phe Val Glu Ala Phe Pro Ile Arg Asp Pro Asn Leu His Ala Ile
    355                 360                 365

```
Glu Met Asp Ser Glu Ile Gln Lys Gln Phe Glu Glu Leu Tyr Ser Leu
    370                 375                 380

Leu Glu Asp Pro Tyr Pro Met Val Arg Ser Thr Gly Ile Leu Gly Val
385                 390                 395                 400

Cys Lys Ile Thr Ser Lys Tyr Trp Glu Met Met Pro Pro Thr Ile Leu
                405                 410                 415

Ile Asp Leu Leu Lys Lys Val Thr Gly Glu Leu Ala Phe Asp Thr Ser
                420                 425                 430

Ser Ala Asp Val Arg Cys Ser Val Phe Lys Cys Leu Pro Met Ile Leu
            435                 440                 445

Asp Asn Lys Leu Ser His Pro Leu Leu Glu Gln Leu Leu Pro Ala Leu
    450                 455                 460

Arg Tyr Ser Leu His Asp Asn Ser Glu Lys Val Arg Val Ala Phe Val
465                 470                 475                 480

Asp Met Leu Leu Lys Ile Lys Ala Val Arg Ala Ala Lys Phe Trp Lys
                485                 490                 495

Ile Cys Pro Met Glu His Ile Leu Val Arg Leu Glu Thr Asp Ser Arg
                500                 505                 510

Pro Val Ser Arg Arg Leu Val Ser Leu Ile Phe Asn Ser Phe Leu Pro
            515                 520                 525

Val Asn Gln Pro Glu Glu Val Trp Cys Glu Arg Cys Val Thr Leu Val
    530                 535                 540

Gln Met Asn His Ala Ala Ala Arg Arg Phe Tyr Gln Tyr Ala His Glu
545                 550                 555                 560

His Thr Ala Cys Thr Asn Ile Ala Lys Leu Ile His Val Ile Arg His
                565                 570                 575

Cys Leu Asn Ala Cys Ile Gln Arg Ala Val Arg Glu Pro Pro Glu Asp
            580                 585                 590

Glu Glu Glu Glu Asp Gly Arg Glu Lys Glu Asn Val Thr Val Leu Asp
            595                 600                 605

Lys Thr Leu Ser Val Asn Asp Val Ala Cys Met Ala Gly Leu Leu Glu
    610                 615                 620

Ile Ile Val Ile Leu Trp Lys Ser Ile Asp Arg Ser Met Glu Asn Asn
625                 630                 635                 640

Lys Glu Ala Lys Leu Tyr Thr Ile Asn Lys Phe Ala Ser Val Leu Pro
                645                 650                 655

Glu Tyr Leu Lys Val Phe Lys Asp Asp Arg Cys Lys Ile Pro Leu Phe
                660                 665                 670

Met Leu Met Ser Phe Met Pro Ala Ser Ala Val Pro Pro Phe Ser Cys
            675                 680                 685

Gly Val Ile Ser Thr Leu Arg Ser Arg Glu Gly Ala Val Asp Lys
    690                 695                 700

Ser Tyr Cys Thr Leu Leu Asp Cys Leu Cys Ser Trp Gly Gln Val Gly
705                 710                 715                 720

His Ile Leu Glu Leu Val Asp Asn Trp Leu Pro Thr Glu His Ala Gln
                725                 730                 735

Ala Lys Ser Asn Thr Ala Ser Lys Gly Arg Val Gln Ile His Asp Thr
                740                 745                 750

Arg Pro Val Lys Pro Glu Leu Ala Leu Val Tyr Ile Glu Tyr Leu Leu
            755                 760                 765

Thr His Pro Lys Asn Arg Glu Cys Leu Leu Ser Ala Pro Arg Lys Lys
    770                 775                 780
```

```
Leu Asn His Leu Leu Lys Ala Leu Glu Thr Ser Lys Ala Asp Leu Glu
785                 790                 795                 800

Ser Leu Leu Gln Thr Pro Gly Gly Lys Pro Arg Gly Phe Ser Glu Ala
            805                 810                 815

Ala Ala Pro Arg Ala Phe Gly Leu His Cys Arg Leu Ser Ile His Leu
        820                 825                 830

Gln His Lys Phe Cys Ser Glu Gly Lys Val Tyr Leu Ser Met Leu Glu
        835                 840                 845

Asp Thr Gly Phe Trp Leu Glu Ser Lys Ile Leu Ser Phe Ile Gln Asp
    850                 855                 860

Gln Glu Glu Asp Tyr Leu Lys Leu His Arg Val Ile Tyr Gln Gln Ile
865                 870                 875                 880

Ile Gln Thr Tyr Leu Thr Val Cys Lys Asp Val Val Met Val Gly Leu
                885                 890                 895

Gly Asp His Gln Phe Gln Met Gln Leu Leu Gln Arg Ser Leu Gly Ile
            900                 905                 910

Met Gln Thr Val Lys Gly Phe Phe Tyr Val Ser Leu Leu Leu Asp Ile
            915                 920                 925

Leu Lys Glu Ile Thr Gly Ser Ser Leu Ile Gln Lys Thr Asp Ser Asp
930                 935                 940

Glu Glu Val Ala Met Leu Leu Asp Thr Val Gln Lys Val Phe Gln Lys
945                 950                 955                 960

Met Leu Glu Cys Ile Ala Arg Ser Phe Arg Lys Gln Pro Glu Glu Gly
                965                 970                 975

Leu Arg Leu Leu Tyr Ser Val Gln Arg Pro Leu His Glu Phe Ile Thr
            980                 985                 990

Ala Val Gln Ser Arg His Thr Asp Thr Pro Val His Arg Gly Val Leu
            995                 1000                1005

Ser Thr Leu Ile Ala Gly Pro Val Val Glu Ile Ser His Gln Leu
    1010                1015                1020

Arg Lys Val Ser Asp Val Glu Leu Thr Pro Pro Glu His Leu
    1025                1030                1035

Ser Asp Leu Pro Pro Phe Ser Arg Cys Leu Ile Gly Ile Ile Ile
    1040                1045                1050

Lys Ser Ser Asn Val Val Arg Ser Phe Leu Asp Glu Leu Lys Ala
    1055                1060                1065

Cys Val Ala Ser Asn Asp Ile Glu Gly Ile Val Cys Leu Thr Ala
    1070                1075                1080

Ala Val His Ile Ile Leu Val Ile Asn Ala Gly Lys His Lys Ser
    1085                1090                1095

Ser Lys Val Arg Glu Val Ala Ala Thr Val His Arg Lys Leu Lys
    1100                1105                1110

Thr Phe Met Glu Ile Thr Leu Glu Glu Asp Ser Ile Glu Arg Phe
    1115                1120                1125

Leu Tyr Glu Ser Ser Ser Arg Thr Leu Gly Glu Leu Leu Asn Ser
    1130                1135                1140

<210> SEQ ID NO 8
<211> LENGTH: 7
<212> TYPE: PRT
<213> ORGANISM: Homo sapiens

<400> SEQUENCE: 8

Gly Val Leu Ser Thr Leu Ile
1               5
```

```
<210> SEQ ID NO 9
<211> LENGTH: 26
<212> TYPE: DNA
<213> ORGANISM: Artificial Sequence
<220> FEATURE:
<223> OTHER INFORMATION: PRIMER

<400> SEQUENCE: 9
cacttctgca gacgccgggt gggaag                                              26

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
cttcccaccc ggcgtctgca gaagtg                                              26

<210> SEQ ID NO 11
<211> LENGTH: 5
<212> TYPE: PRT
<213> ORGANISM: Homo sapiens

<400> SEQUENCE: 11

Val Leu Ser Thr Leu
1               5
```